United States Patent
Davies et al.

(10) Patent No.: US 9,389,182 B2
(45) Date of Patent: Jul. 12, 2016

(54) LABELING OF PROTEINS WITH THE FLUOROPHORE 7-AMINO-4-METHYLCOUMARIN (AMC) GENERATED NOVEL PROTEOLYTIC SUBSTRATES

(75) Inventors: Kelvin J. A. Davies, Pasadena, CA (US); Andrew M. Pickering, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 586 days.

(21) Appl. No.: 13/600,908

(22) Filed: Aug. 31, 2012

(65) Prior Publication Data

US 2013/0059321 A1    Mar. 7, 2013

Related U.S. Application Data

(60) Provisional application No. 61/529,381, filed on Aug. 31, 2011.

(51) Int. Cl.
*C12P 19/46* (2006.01)
*G01N 21/64* (2006.01)

(52) U.S. Cl.
CPC ............ *G01N 21/64* (2013.01); *G01N 21/6428* (2013.01)

(58) Field of Classification Search
CPC ..... C07C 231/12; G01N 21/6428; C12N 9/14
USPC ................... 435/18, 23, 7; 540/500
See application file for complete search history.

(56) References Cited

PUBLICATIONS

Sojka et al.Parasites and vectors 2008, I:7, pp. 1-13.*
Partanen et al. Biochem. J. 2003, 369, pp. 55-62.*
Venpure; a circulation from Rohm and HAAS, 2003, 10.*
Baxter et al. Reductive Aminations of Carbonyl Compounds with Borohydride, Organic Reactions, 2002, p. 1-178.*
Table V of Baxter et al.*
ClonTech circular Caspase Fuoroscent Assay Kits User manual Sep. 1, 2003.*
Promega Technical bulletin CasPACETM Assay System Fluorometric Jan. 2007.*
Laan et al. Appld & Environ. Microbiol.1991, 57, pp. 2586-2590.*
Table V of Baxter et al., Reductive amination of carbonyl compounds with Borohydride, Organic reactions p. 1-178, 2002.*

* cited by examiner

*Primary Examiner* — Md. Younus Meah
(74) *Attorney, Agent, or Firm* — Brooks Kushman P.C.

(57) ABSTRACT

A method of measuring the degradation of intact proteins includes a step of providing a protein substrate having one or more free or exposed carboxyl groups and then reductively attaching 7-amino-4-methylcoumarin (AMC) to the protein substrate with a reducing agent. The protein substrate is contacted in a test solution with one or more proteolytic enzymes that degrade the protein substrate. The amount of AMC attached to the protein substrate is then determined by monitoring the fluorescence of free 7-amino-4-methylcoumarin that is formed during degradation of the protein substrate to protein fragments.

19 Claims, 13 Drawing Sheets

Proposed reaction between AMC and the free carbonyl
groups of a protein (R-) mediated by sodium cyanoborohydride

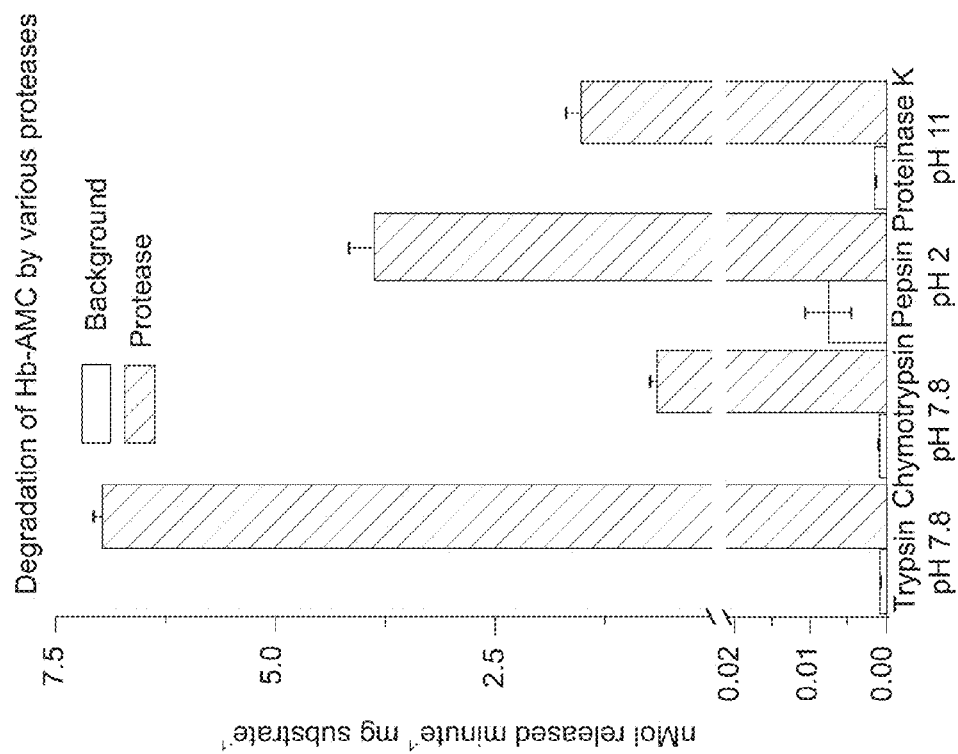
Fig. 6C
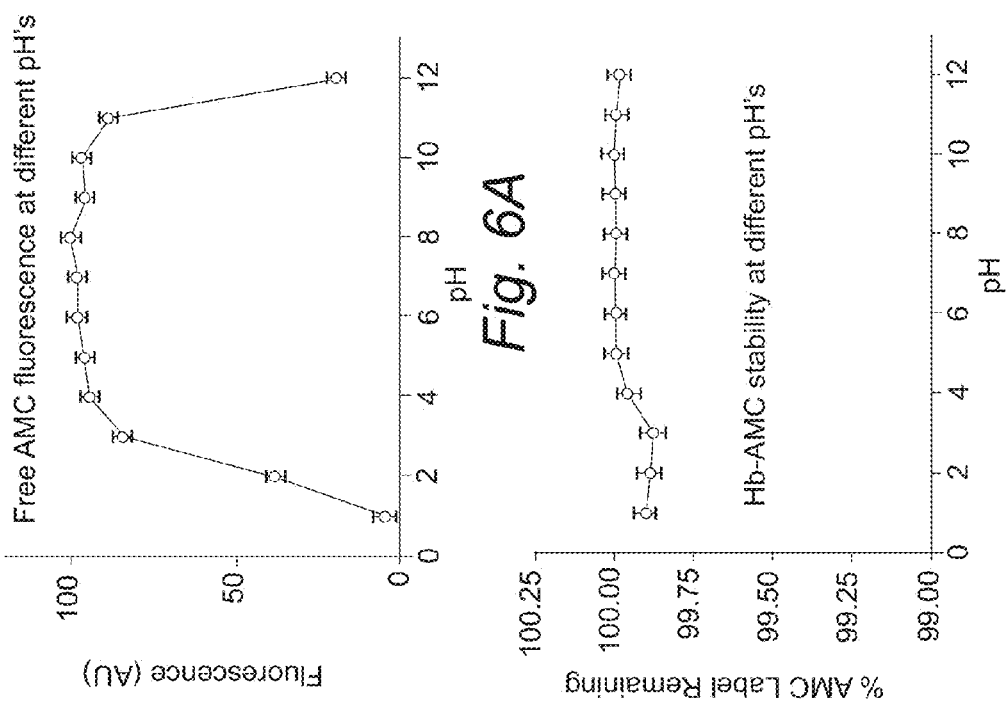
Fig. 6A
Fig. 6B

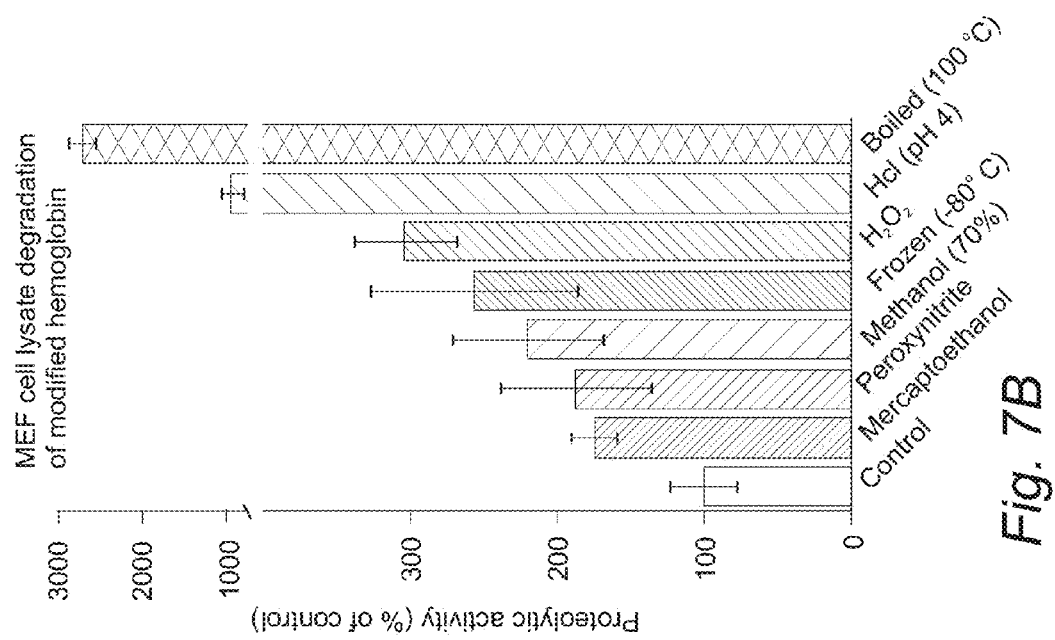
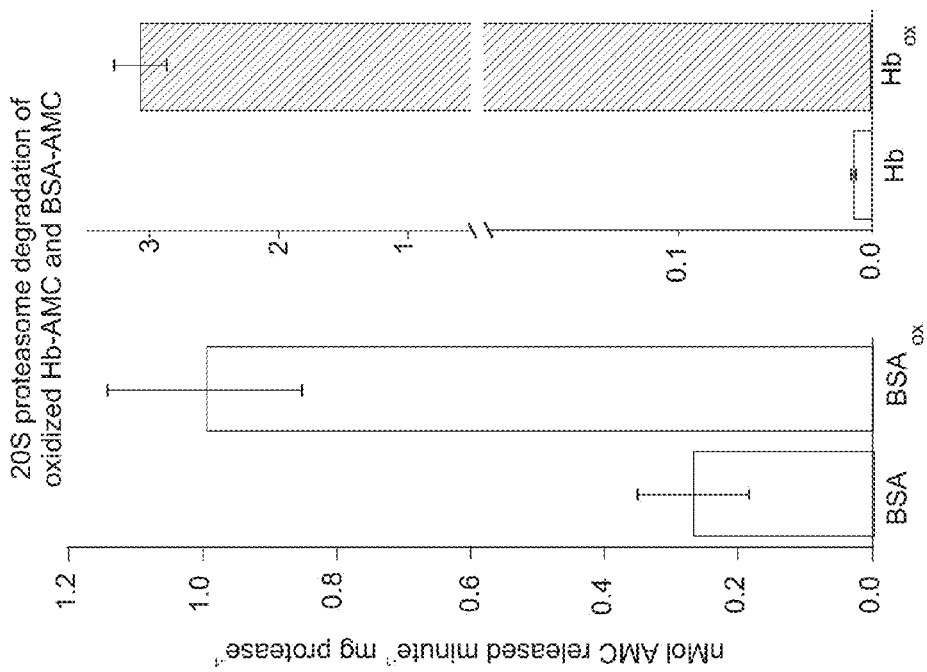
Fig. 7B
Fig. 7A

US 9,389,182 B2

LABELING OF PROTEINS WITH THE FLUOROPHORE 7-AMINO-4-METHYLCOUMARIN (AMC) GENERATED NOVEL PROTEOLYTIC SUBSTRATES

CROSS REFERENCE TO RELATED APPLICATIONS

This application claims the benefit of U.S. provisional application Ser. No. 61/529,381 filed Aug. 31, 2011, the disclosure of which is incorporated in its entirety by reference herein.

STATEMENT REGARDING FEDERALLY SPONSORED RESEARCH OR DEVELOPMENT

The invention was made with Government support under Grant No. RO1-ES003598, and by ARRA Supplement 3RO1-ES 003598-22S2, both from the NIH/NIEHS to KJAD. The Government has certain rights to the invention.

TECHNICAL FIELD

In at least one aspect, the present invention provides a method of measuring protein degradation.

BACKGROUND OF THE INVENTION

The free radical/oxidative stress field has a long history of papers devoted to lipid peroxidation and DNA oxidation, but protein oxidation and, particularly, altered proteolytic susceptibility have not been studied by very many laboratories. Reasons for this apparent reluctance to measure protein degradation as a consequence of oxidative stress may well include the difficulty, expense, and (even) danger of the available methods. Basically, until now, if one wanted to study how oxidation may change the proteolytic susceptibility of any given purified protein (or mixture of protein substrates), one needed to be willing to use radioactive labels, or tracers. For many laboratories, the complicated protein labeling techniques, radioactive isotope training and licenses or permits, radioactive waste disposal problems, potential dangers to lab workers, and high costs of radioactive techniques have proven to be major barriers to the study of protein oxidation and proteolysis.

The use of $^3H$ and $^{14}C$ labeling of proteins by in vitro reductive methylation has become an important tool to measure the proteolytic degradation of a wide range of protein substrates by purified proteolytic enzymes, cell lysates, and cell extracts. Such 3H and $^{14}C$ labeled protein substrates are also widely used to assess the effects of protein modifications, such as denaturation, oxidation, methylation, acetylation, etc., on proteolytic susceptibility and rates of turnover. In addition, the specificity of various proteolytic enzymes for putative substrates has frequently been tested using $^3H$ and $^{14}C$ labeled proteins. The process of in vitro reductive methylation with $^3H$ and $^{14}C$, however, does have a number of drawbacks. The use of radioactive materials, with all the attendant exposure risks for experimenters and their colleagues, and the difficulties and ethical considerations of radioactive waste procedures rank high on the list of drawbacks. Experimenters must maintain radioactive use permits that require frequent evidence of ongoing training and compliance. Additionally, the costs both of purchasing radionucleotides and of disposing of them are extremely high.

Proteolytic assays with $^3H$ and $^{14}C$ labeled protein substrates require a labor-intensive TCA precipitation step, so that undegraded (TCA-insoluble) proteins can be separated from TCA-soluble degradation products. This further increases the volume of radioactive waste, limits the number of samples that may be analyzed, increases experimental error, and forces an absolute endpoint to the assay with the result that continuous time courses cannot be measured. These drawbacks have effectively limited the preparation and use of radio-labeled protein substrates to study protein degradation to those laboratories where proteolysis is the major topic.

Fluorometric peptidase assays, in which a fluorophore covalently linked to a small peptide sequence is cleaved by a protease/proteinase, provides a solution to all the above radiolabeling problems, and small fluorogenic peptides are widely used to measure peptidase activities. Such fluorogenic peptidase measurements are based on the increase in fluorescence as the fluorophore is released from the peptide by proteolytic cleavage. TCA precipitation is not required, thus enabling continuous readings to be made, as well as permitting a greater number of assays to be performed. While this technology has been highly valuable in measuring the cleavage of short peptide sequences, it is only a primitive model with which to test the activities of complete proteinases which target whole proteins rather than short peptide sequences. Additionally many proteinases are selective for various modified forms of their protein substrates, and such selectivity cannot be measured by peptide hydrolysis.

A solution would seem to be that of adapting the fluorescence labeling technique for peptides to work with intact proteins, but there has been limited success in modifying this technology to measure the degradation of whole proteins. Two techniques have been described for attaching fluorophores onto proteins. FITC labeling has been used to label casein, hemoglobin (Hb), and bovine serum albumin (BSA). However, FITC-labeled proteins are highly unstable and so must be precipitated and stored in 50% ammonium sulfate and then transferred out of solution, just before use. These steps are major drawbacks and present considerable contamination risks as well as limiting the time over which assays can be performed. The assay is further limited by a strong dependency on pH for the sensitivity of the fluorophore, making assays of strongly acidic proteases such as pepsin, or strongly alkaline proteases such as proteinase K, impractical. In addition, for measuring proteolysis, this technique is, like radiolabeling, limited by the requirement for TCA precipitation, which makes it labor intensive, error prone, and extremely limited to small-size experiments. The second technique involves labeling of either casein or BSA with BODIPY. This technique provides a number of advantages over both FITC labeling and radiolabeling, though it also has several drawbacks. For example, BODIPY has a very small separation between excitation and emission wavelengths (503 nm/512 nm) compared to other fluorophores such as 7-amino-4-methylcoumarin (AMC; 365 nm/444 nm), which makes it extremely difficult to detect the signal without highly specialized equipment. The label is relatively large and complex (389-634 Da, depending on type of BODIPY label) compared to the small [$^3H$]formaldehyde label (32 Da) used in radiolabeling; this raises some concerns about modification of the protein during BODIPY labeling. BODIPY is also relatively expensive for very small quantities, compared with other fluorophores. Finally, there are only a small number of assays for which BODIPY has been described. Thus, most studies of protein degradation continue to rely on in vitro radiolabeling ([$^3H$] or [14C]) of purified protein substrates, using the technique of reductive methylation developed by Jentoft and Dearborn (Jentoft, N.; Dearborn, D. G. *Labeling of proteins by reductive methylation using sodium cyanoborohydride.* J. Biol. Chem. 254:4359-4365; 1979).

Accordingly, since in vitro radio-labeling of protein substrates is desirably avoided and neither FITC—nor the BODIPY-labeling alternatives appear entirely suitable, there is a need for improved methods of labeling protein substrates.

SUMMARY OF THE INVENTION

In at least one embodiment, the present invention provides a labeling technique that is used to study the degradation of intact proteins. The present method comprises providing a protein substrate onto which 7-amino-4-methylcoumarin (AMC) is bound using a reducing agent. The protein substrate is then contacted in a test solution with one or more proteolytic enzymes that degrade the protein substrate. The fluorescence of AMC is quenched through attachment to the protein however with the cleavage of the protein substrate (though the action of proteases) AMC fluorescence is partially restored. This enables proteolytic activity to be approximated through measurements of the change in fluorescence of the sample. The method of this embodiment utilizes a variation of reductive methylation which is an efficient and relatively mild procedure by which to attach a label to a protein, utilizing free or exposed carboxyl group(s). The fluorophore 7-amino-4-methylcoumarin (AMC) is a small molecule (MW 175). The method of the present embodiment provides a novel technique by which an inexpensive and stable AMC fluorophore-protein complex is formed both quickly and simply by reductive labeling. As set forth below, the present embodiment is applicable to a wide range of protein substrates. Moreover, the method can be used to measure proteolytic susceptibility with high sensitivity, comparable to that achieved with radio-labeled proteins. Advantageously, AMC-protein adducts are stable to oxidation and various other denaturing conditions, and can be used to measure the increased proteolytic susceptibility of modified proteins. The present embodiment, offers a sensitive, inexpensive, rapid, radiation-free alternative to $^3$H or $^{14}$C labeling, which also allows truly continuous monitoring of proteolysis, since no TCA precipitation step is required, and fluorescence can be monitored in the same sample for many hours.

In another embodiment, a method for monitoring the degradation of a protein is provided. The present method comprises providing a protein substrate onto which a coumarin derivative is bound using a reducing agent. The coumarin derivative is described by the following formula:

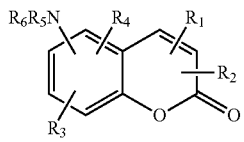

wherein:
$R_1$, $R_2$ are each independently hydrogen, $C_{1-10}$ alkyl, $C_{1-10}$ alkoxy, $C_{3-10}$ amide, $C_{4-10}$ diamide, $C_{3-10}$ ester, $C_{4-10}$ diester, $C_{6-10}$ aryl, or $C_{6-10}$ heteroaryl;

$R_3$, $R_4$ are each independently hydrogen, $C_{1-10}$ alkyl, $C_{1-10}$ alkoxy, $C_{2-10}$ carboxy, $C_{3-10}$ amide, $C_{4-10}$ diamide, $C_{3-10}$ ester, $C_{4-10}$ diester, $C_{6-10}$ aryl, or $C_{6-10}$ heteroaryl; and $R_5$, $R_6$ are each independently hydrogen or $C_{1-5}$ alkyl.

The protein substrate is then contacted in a test solution with one or more proteolytic enzymes that degrade the protein substrate. The fluorescence of the coumarin derivative is quenched through attachment to the protein however with the cleavage of the protein substrate (though the action of proteases) coumarin derivated fluorescence is partially restored. This enables proteolytic activity to be approximated through measurements of the change in fluorescence of the sample.

BRIEF DESCRIPTION OF THE DRAWINGS

Exemplary embodiments of the present invention will become more fully understood from the detailed description and the accompanying drawings, wherein:

FIG. 6. pH Profile of Fluorescence, Stability, and Proteolytic Susceptibility of Free AMC and Hb-AMC. (A) The fluorescence of free AMC was measured in proteolysis buffer over a wide range of pH conditions. (B) Samples of Hb-AMC were incubated over a range of pH conditions for 4 hr. The pH of each sample was then adjusted to pH 7.8 and AMC fluorescence was measured. Results are expressed as a percent of total AMC label originally incorporated into the Hb-AMC complex which was (separately) assessed by exhaustive proteolytic digestion of Hb-AMC, by incubation with 500 µM trypsin for 4 hours. (C) Hb-AMC was incubated with 100 µM trypsin, 10 µM chymotrypsin, 100 µM pepsin, or 100 µM proteinase K (at the pH shown for each protease) for 4 hr at 37° C. and proteolysis was measured by AMC release, as described in the legend to FIG. 4A. Values in all panels are means±SE's, n=3; and FIG. 7. Proteolytic Susceptibility of Modified AMC-labeled Proteins. (A) The capacity of 20S proteasome to degrade both the native and oxidized forms of Hb-AMC and BSA-AMC was measured. For both assays, 1 µg/ml of purified 20S proteasome was combined with 10 µg/ml of Hb-AMC, Hbox-AMC, BSA-AMC, or BSAox-AMC and incubated for 4 hr at 37° C. Protein degradation was then measured as per FIG. 4. Hbox-AMC, and BSAox were prepared by treating Hb-AMC and BSA-AMC with 1.0 mM H2O2 followed by extensive dialysis. (B) The Capacity of MEF cell lysates to degrade various modified forms of Hb-AMC was measured. Hb-AMC was modified by incubation with dilute HCl at pH 4, 10% 2-mercaptoethanol, 70% methanol, 1 mM peroxynitrite, or 1 mM H2O2, or was boiled at 100° C. for 60 minutes, or subjected to freeze-thawing at −80° C. The substrates were then extensively dialyzed and incubated with 150 µg/ml of MEF cell lysates for 4 hr. In both panels, values are means±SE's, n=3.

DETAILED DESCRIPTION OF EXEMPLARY EMBODIMENTS

Figure 1A:
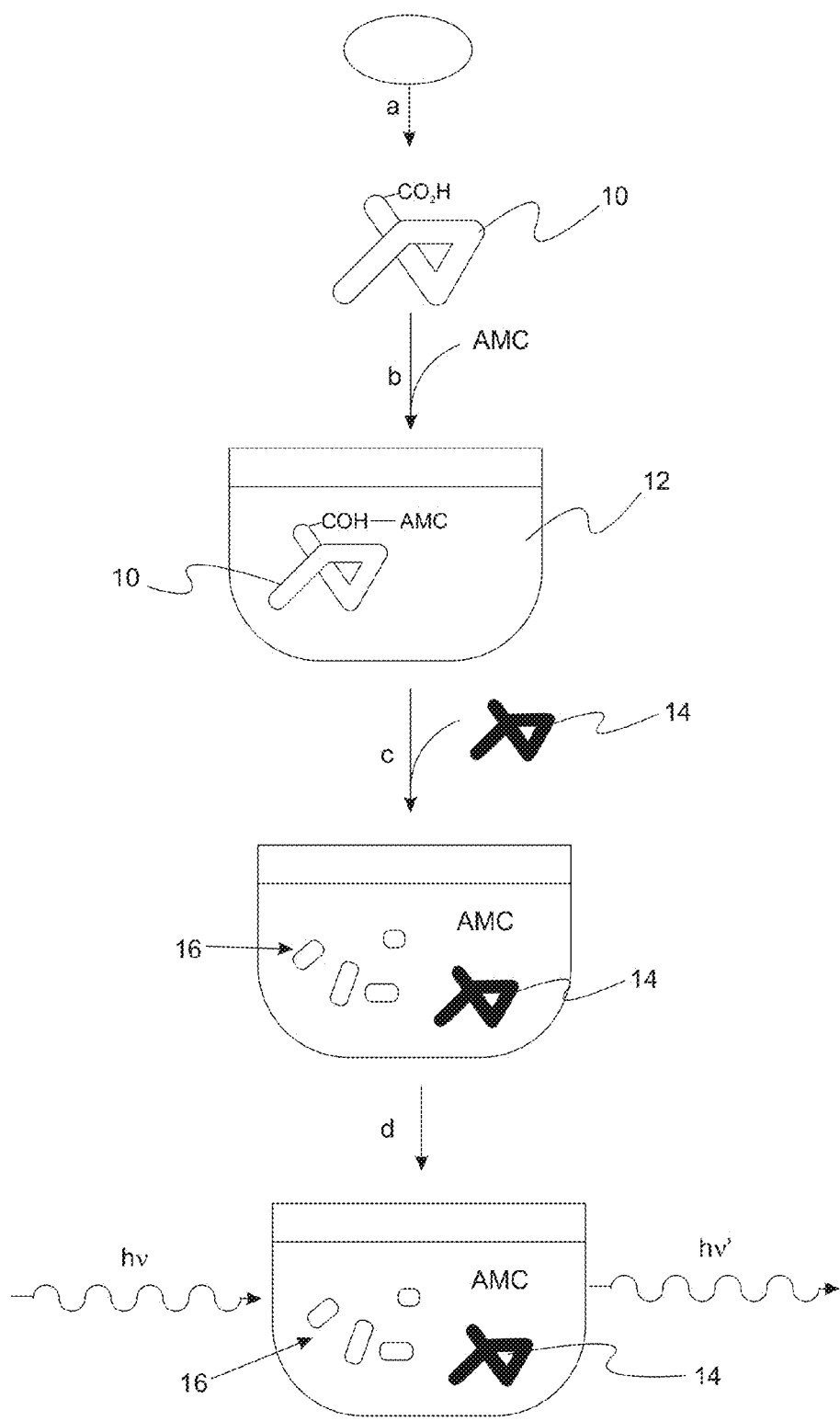
FIG. 1A provides a schematic flowchart of a method for measuring the degradation of intact proteins.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The abbreviations used herein are: AMC, the fluorophore 7-amino-4-methylcoumarin; TCA, trichloloracetic acid; FITC, Fluorescein isothiocyanate; BSA, bovine serum albumin; Hb-AMC, AMC-labeled hemoglobin; BSA-AMC, AMC-labeled bovine serum albumin; SOD-AMC, AMC-labeled superoxide dismutase; H2O2, hydrogen peroxide; MEF, murine embryonic fibroblasts; [³H]Hb, tritium-labeled hemoglobin; Hbox, oxidized hemoglobin; BSAox, oxidized BSA; TCA, trichloroacetic acid; sulfo-NHS-acetate, sulfo-N-hydroxysulfosuccinimide-acetate.

Figure 1B:
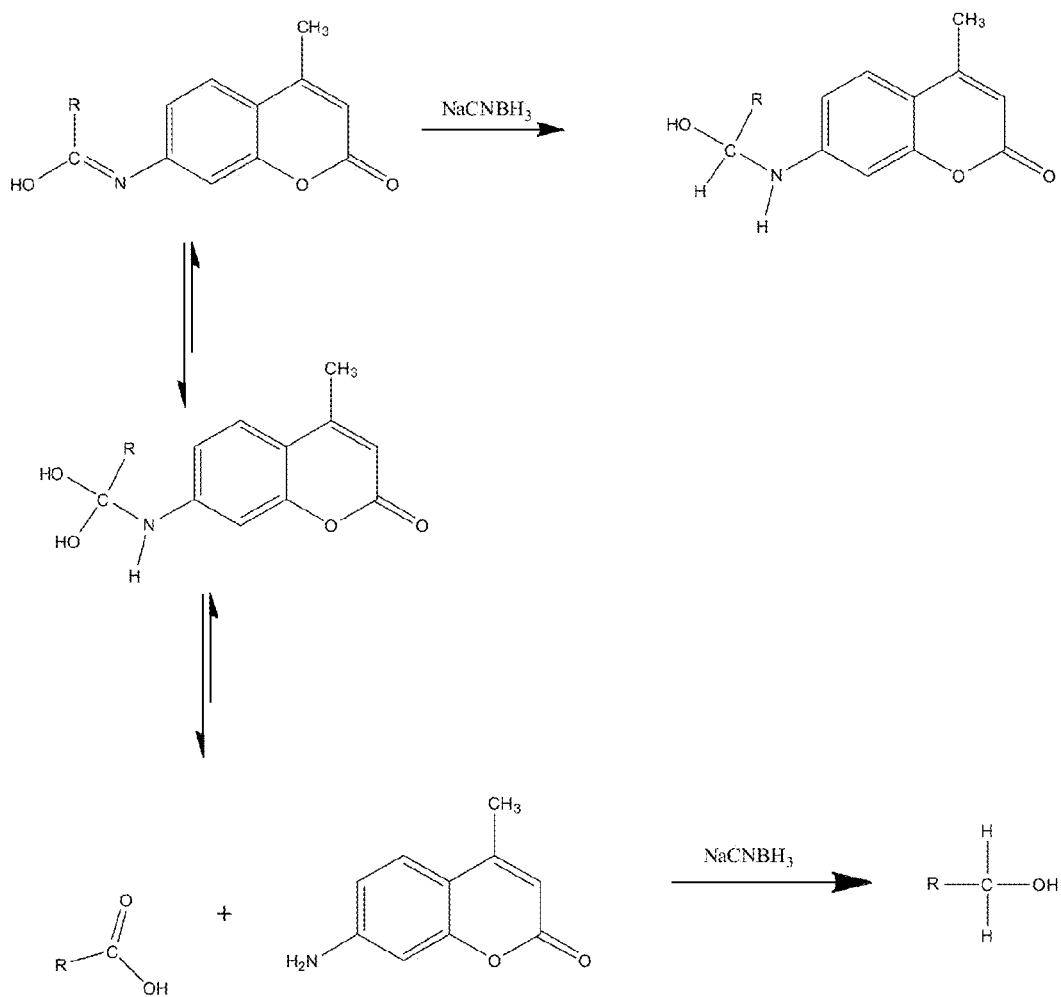
FIG. 1B. Proposed Reaction Between AMC and the Free Carboxyl Groups of Proteins (R—), Mediated by Sodium Cyanoborohydride.

In an embodiment of the present invention, a method for measuring the degradation of intact proteins. FIG. 1A provides a schematic flowchart illustrating the method. FIG. 1B provides a proposed reaction between AMC and the free carboxyl groups of proteins mediated by sodium cyanoborohydride. Although the present invention is not limited by any particular mechanism for operation, it is speculated that AMC bonds onto or associates with exposed carboxyl groups. In FIG. 1B, "R" is the remaining part of the protein that is attached to the carboxyl group undergoing this reaction. The present method comprises providing a protein substrate 10 having one or more free or exposed carboxyl group (step a) and then reductively attaching a coumarin derivative, and in particular, 7-amino-4-methylcoumarin (AMC) to the protein substrate with a reducing agent (e.g., sodium cyanoborohydride (NaCNBH₃), NaBH₄, and the like) in step b). In step c), the protein substrate 10 is then contacted in a test solution 12 with one or more proteolytic enzymes 14 that degrade the protein substrate into protein fragments 16 and into free coumarin derivative, and in particular, free AMC (i.e., not bonded to protein). In step c), the amount of coumarin derivative, and in particular, AMC attached to the protein substrate is then determined by monitoring the fluorescence during degradation. In a refinement, this fluorescence comes from free 7-amino-4-methylcoumarin or 7-amino-4-methylcoumarin that is bound to short (cleaved) peptides (<500 Da) that are formed during degradation of the protein substrate. The method of this embodiment utilizes a variation of reductive methylation which is an efficient and relatively mild procedure by which to attach a label to a protein, utilizing free or exposed carboxyl group(s).

The measured fluorescence is compared to a standard curve to determine the amount of protein substrate. In particular, the measured fluorescence is compared to a standard curve of known concentration of free coumarin derivative, and in particular, free AMC to quantify the moles of coumarin derivative (e.g. AMC) released into solution. In a refinement, the known concentration of free coumarin derivative, and in particular, AMC is between 5 nM (nanomolar) and 5 mM (millimolar).

As set forth above, the variations of the present embodiment use coumarin derivative, and in particular, AMC. Such derivatives are represented by the following formula:

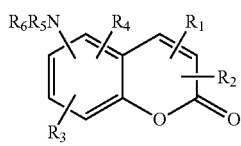

wherein:

$R_1$, $R_2$ are each independently hydrogen, $C_{1-10}$ alkyl (e.g., methyl, ethyl, propyl, etc), $C_{1-10}$ alkoxy (methoxy, ethoxy, propoxy, etc.), $C_{1-10}$ perfluoroalkyl (e.g, trifluoromethyl), $C_{3-10}$ amide, $C_{4-10}$ diamide, $C_{3-10}$ ester, $C_{4-10}$ diester, $C_{6-10}$ aryl, $C_{6-10}$ heteroaryl, and the like;

$R_3$, $R_4$ are each independently hydrogen, $C_{1-10}$ alkyl (e.g., methyl, ethyl, propyl, etc), $C_{1-10}$ alkoxy (methoxy, ethoxy, propoxy, etc.), $C_{1-10}$ perfluoroalkyl (e.g, trifluoromethyl), $C_{2-10}$ carboxy (methoxy, ethoxy, propoxy, etc.), $C_{3-10}$ amide, $C_{4-10}$ diamide, $C_{3-10}$ ester, $C_{4-10}$ diester, $C_{6-10}$ aryl, $C_{6-10}$ heteroaryl, and the like; and $R_5$, $R_6$ are each independently hydrogen or $C_{1-5}$ alkyl (e.g., methyl, ethyl, propyl, etc). In a refinement, $R_1$, $R_2$ $R_3$, $R_4$ are each independently —$CO_2H$, —$CH_2 CO_2H$, nitro, hydroxyl, isopropyl, benzyl, acetyl, chloro, fluoro, glucoxy, geranoxy, Specific examples of coumarin derivatives include but are not limited to:

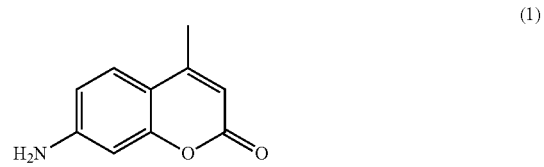

(1)

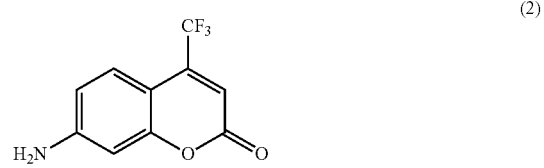

(2)

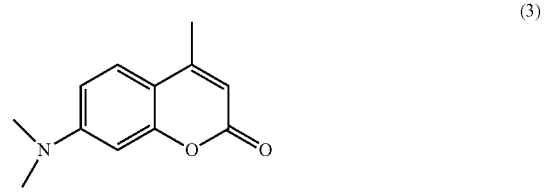

(3)

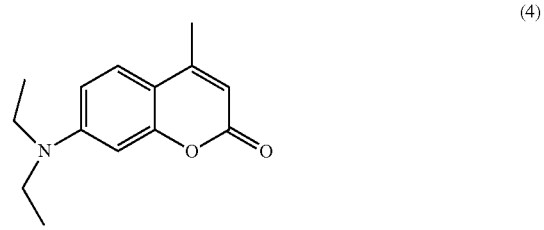

(4)

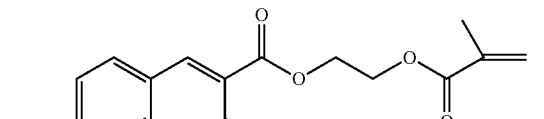

(6)

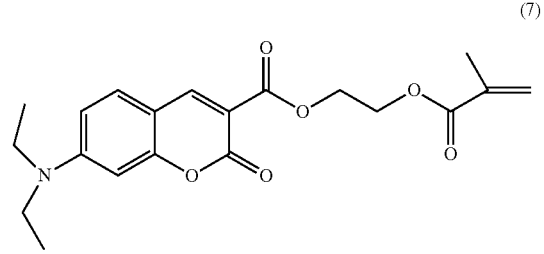

(7)

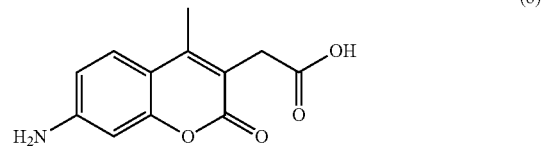

(8)

-continued

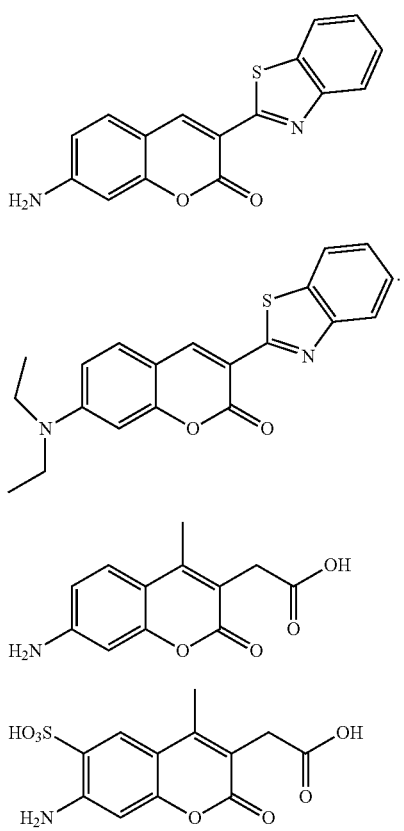

In a variation of the present embodiment, the protein substrate is a purified proteolytic enzymes. In another refinement, the protein substrate is obtained from cell lysates or cell extracts. Typically, the protein substrate has a molecular weight from about 10 kDa (kilodalton) to about 300 kDa. Specific examples for the protein substrate, include, but are not limited to, bovine serum albumin (BSA), catalase, hemoglobin, and superoxide dismutase (SOD). Similarly, any number of proteolytic enzymes know to those skilled in the art may be used to practice the present invention. Specific examples include, but are not limited to, pepsin, proteinase K, trypsin, and chymotrypsin.

The method of the present invention is not limited by the temperature or pH of the test solution. The pH may be set to any value that is compatible with the protein substrate and proteases. In a refinement, the test solution has a pH from about 2 to about 11. Typically, the method of the present embodiment is carried out at or near room temperature. In a refinement, the method is carried out at temperatures from about 10 to 40° C.

Similarly, the present embodiment is not substantially limited by the range in concentrations of the protein substrate and the proteolytic enzyme. In a refinement, the proteolytic enzyme is present in an amount from about 320 nM to about 1 mM of the test solution. In another refinement, the protein substrate is present in the test solution in an amount from about 25 ng per milliliter to about 0.5 µg per milliliter.

As set forth above, the method includes a step in which the protein substrate is degraded into protein fragments. Typically, greater than 50 percent of the protein fragments are smaller than 500 Da. In a refinement, an amount greater than or equal to 80 percent of the protein fragments are smaller than 500 Da. In another refinement, about 15% are particles between 500 Da and 5 kDa, and only some 5% of the signal comes from peptides larger than 5 kDa.

As set forth above, the method includes a step of measuring the fluorescence. In a refinement, the fluorescence is initiated by excitation with light having a wavelength from 360 to 420 nanometers (depicted by hv in FIG. 1A). Typically, a laser light source may be used for this excitation. A wavelength of about 390 nm is found to be particularly useful. Typically, the fluorescence is measured at a wavelength from about 430 to about 450 nanometers (depicted by hv' in FIG. 1A). A wavelength of about 444 nm is found to be particularly useful for this purpose. The mount of fluorescence is measured by measuring the intensity of light at this wavelength or wavelength range by methods known in the art. The fluorescence may be continuously monitored or it may be measure in intervals of a few seconds to several minutes depending on the rate of degradation of the protein substrate. An interval of 10 minutes has been found useful in the experiments set forth below.

The following examples illustrate the various embodiments of the present invention. Those skilled in the art will recognize many variations that are within the spirit of the present invention and scope of the claims.

Experimental Procedures

AMC Labeling of Protein Substrates

The protein substrates used for AMC labeling were as follows: Hemoglobin from Sigma-Aldrich (St Louis, Mo., USA) catalogue #H-2500, Superoxide Dismutase from Calbiochem (San Diego, Calif., USA) catalogue #574594, Catalase from Calbiochem (San Diego, Calif., USA) catalogue #219001, and Bovine Serum Albinum from thermo-Fisher (Waltham, Mass., USA) catalogue #BP1605-100. In all cases, 5 mg of protein were dissolved in 1 ml of 0.1M Hepes buffer to which was added 500 µM of AMC (Calbiochem, San Diego, Calif., USA, catalogue #164545), as well as 20 mM sodium cyanoborohydride (final concentration) from Sigma-Aldrich (St Louis, Mo., USA, catalogue #58628-25G). Solutions were incubated at room temperature for 2 hours, then extensively dialyzed though a 10,000 M.W.C.O centrifugal filter (Millipore, Carrigtwohil, Ireland, catalogue #4321) and a buffer exchange was performed with proteolysis buffer (50 mM Tris/HCl pH7.8, 20 mM KCl, 5 mM magnesium acetate, 0.5 mM DTT). Protein content was then determined using the BCA assay kit (Thermo Scientific, Rockford, Ill., USA, catalogue #PI-23225).

In some experiments samples were pre-treated with either N-(3-Dimethylaminopropyl)-N'-ethylcarbodiimide hydrochloride (Sigma-Aldrich, MO, USA, catalogue#E6383-1G) to block free protein carboxyl groups, with sulfo-N-hydroxysulfosuccinimide-acetate (Pierce, Rockford, Ill., USA, catalogue #26777) to block free protein amino groups, or with tryptamine (Sigma-Aldrich, MO, USA, catalogue#193747-10G) to disrupt potential non-covalent interactions in protein hydrophobic pockets.

[$^3$H] Labeling of Protein Substrates

Tritium-labeled hemoglobin ([$^3$H]Hb) and BSA ([$^3$H]BSA) were generated in vitro as previously described using the [$^3$H]formaldehyde and sodium cyanoborohydrate method of Jentoft and Deaborn. Proteins were then extensively dialyzed. (Davies, K. J. A. *Degradation of oxidized proteins by the 20S proteasome. Biochimie* 83:301-310; 2001; Shringarpure, R.; Grune, T.; Mehlhase, J.; Davies, K. J. A. *Ubiquitin conjugation is not required for the degradation of oxidized proteins by proteasome.* J. Biol. Chem. 278:311-318; 2003; Grune, T.; Reinheckel, T.; Joshi, M.; Davies, K. J. A. *Pro-* teolysis in cultured liver epithelial cells during oxidative stress: role of the multicatalytic proteinase complex, proteasome. J. Biol. Chem. 270:2344-2351; 1995; Grune, T.; Reinheckel, T.; Davies, K. J. A. *Degradation of oxidized proteins in K562 human hematopoietic cells by proteasome.* J. Biol. Chem. 271:15504-15509; 1996; Ullrich, O.; Reinheckel, T.; Sitte, N.; Hass, R.; Grune, T.; Davies, K. J. A. Poly-ADP ribose polymerase activates nuclear proteasome to degrade oxidatively damaged histones. Proc. Natl. Acad. Sci. U.S.A. 96:6223-6228; 1999; Jentoft, N.; Dearborn, D. G. *Labeling of proteins by reductive methylation using sodium cyanoborohydride.* J. Biol. Chem. 254:4359-4365; 1979, the entire disclosures of these references are hereby incorporated by reference).

Cell Culture—Murine Embryonic Fibroblasts

Murine embryonic fibroblasts (MEF) from ATCC (Manassas, Va., USA, catalogue CRL-2214) were grown in Dulbecco's Modified Eagle's Medium (DMEM, Mediatech, Manassas, Va., catalogue #10-013-CV) supplemented with 10% Fetal Bovine Serum (Hyclone, Logan, Utah, catalog #SH30070.03). Cells were incubated at 37° C. under 5% $CO_2$ and ambient oxygen. To generate cell lysates, MEF were grown to confluence then washed twice with PBS, cells were then scraped using a cell lifter, and centrifuged at 5,000 g for 5 minutes. The cells were then re-suspended in proteolysis buffer and subjected to 3 freeze-thaw cycles at −20° C. The lysates were then centrifuged at 10,000 g for 10 minutes, after which the supernatants were retained (the pellets discarded) and protein content was determined by BCA assay.

Proteolysis Assay—Common Procedures

Proteolysis was measured by incubation of 1 µg of AMC-labeled protein substrate or [$^3$H]-labeled protein substrate in 100 µl of proteolysis buffer containing either dissolved Trypsin (VWR, West Chester, Pa., USA, catalogue #100504-332), Chymotrypsin (Sigma-Aldrich, MO, USA, catalogue #C-7762), Pepsin (Thermo-Fisher, Waltham, Mass., USA, catalogue #P53), Proteinase K (Oncor, Gaithersburg, Md., USA, catalogue #S4508), purified 20S proteasome (Biomol, Plymouth Meeting, Pa., USA, catalogue #PW8720-0050), or lysate generated from MEF cells as above. In each experiment, pH was adjusted appropriately for the proteinase studied, and samples were incubated at 37° C. for 4 hours.

Proteolysis of AMC-Labeled Proteins by Fluorescence Assay

This procedure was used with AMC-labeled proteins. It should be noted that free AMC is soluble in water, and that it fluoresces strongly. AMC adducted to proteins, by reductive methylation, fluoresces only minimally (just enough to detect weakly in gel assays) but when liberated by proteolysis it again fluoresces strongly. During incubations described above under "Proteolysis Assay—Common Procedures," fluorescence was measured every 10 minutes at an emission wavelength of 444 nM, with excitation at 390 nm, in a Fluoroskan Ascent Microplate Fluorometer (Thermo Fisher, Waltham, Mass., USA, catalogue #5210480). Fluorescence emission was compared with a standard curve of the fluorescence of known concentrations of free AMC, between 5 nM and 5 mM, to quantify the moles of AMC released into solution.

Proteolysis of [$^3$H]-Labeled Proteins by Radioactive Liquid Scintillation Assay After incubations described above under "Proteolysis Assay—Common Procedures," remaining intact protein was precipitated by addition of 20% trichloroacetic acid and 3% BSA (as carrier) as previously described. (Shringarpure, R.; Grune, T.; Mehlhase, J.; Davies, K. J. A. *Ubiquitin conjugation is not required for the degradation of oxidized proteins by proteasome.* J. Biol. Chem. 278:311-318; 2003; Pickering, A. M.; Koop, A. L.; Teoh, C. Y.; Ermak, G.; Grune, T.; Davies, K. J. A. *The immunoproteasome, the 20S proteasome, and the PA28αβ proteasome regulator are oxidative stress-adaptive proteolytic complexes.* Biochem. J. 432:585-594; 2010; Reinheckel, T.; Grune, T.; Davies, K. J. A. *The measurement of protein degradation in response to oxidative stress.* Methods Mol. Biol. 99:49-60; 2000; Grune, T.; Reinheckel, T.; North, J. A.; Li, R.; Bescos, P. B.; Shringarpure, R.; Davies, K. J. A. *Ezrin turnover and cell shape changes catalyzed by proteasome in oxidatively stressed cells.* FASEB J. 16:1602-1610; 2002; Pacifici, R. E.; Davies, K. J. A. *Protein degradation as an index of oxidative stress.* Methods Enzymol. 186:485-502; 1990; the entire disclosures of these references are hereby incorporated by reference).

Percent protein degraded was estimated by release of acid soluble counts into the TCA supernatants, measured by liquid scintilatation, in which percent protein degraded=(acid-soluble counts−background counts)×100.

SDS and Native Page Gels

For SDS Page gels, samples were mixed with 25% Nupage loading Dye (Invitrogen, Carlsbad, Calif., USA, catalogue#NP0007) containing 5% 2-mercaptoethanol, Samples were boiled for 3 minutes then added to a 12% Tris-glycine SDS page gel. (VWR, West Chester, Pa., USA, catalogue#12001-042) and run at 80V for 2 hr. In experiments where gel fluorescence was analyzed, gels were placed in a chamber and exposed to an excitation wavelength of 365 nM. Silver staining was performed using silverSNAP stain kit II (Waltham, Mass., USA, catalogue#24612), as described in the product manual. For Commassie staining, gels were incubated in commassie stain (0.1% Coomassie blue R350, 10% methanol 10% acetic acid) for 30 minutes and then repeatedly washed in de-stain solution (10% Methanol, 10% acetic acid) until excess stain was removed. In the case of Native Page Gels, samples were mixed with a loading buffer of 25% glycerol/Brilliant Blue solution. Samples were then run on a 12% Native gels prepared exactly as described in the instructions for preparation of a 12% SDS-Page gels in (Biorad, Hercules, Calif., USA, Catalogue#161-0154) with the exception that 10% SDS was not added to the gel.

Results

Reductively Binding AMC to Protein Carboxyl Groups

Although the represent invention is not limited to any particular mechanism for operation, it is hypothesized that sodium cyanoborohydride ($NaCNBH_3$), which is commonly used to label proteins with either $H^3$ or $C^{14}$ linked formaldehyde, can be used to label proteins with AMC by promoting the formation of a carbon-nitrogen bond between the exposed amine group in the AMC molecule and free carboxyl groups of target proteins (FIG. 1).

Figure 2A:
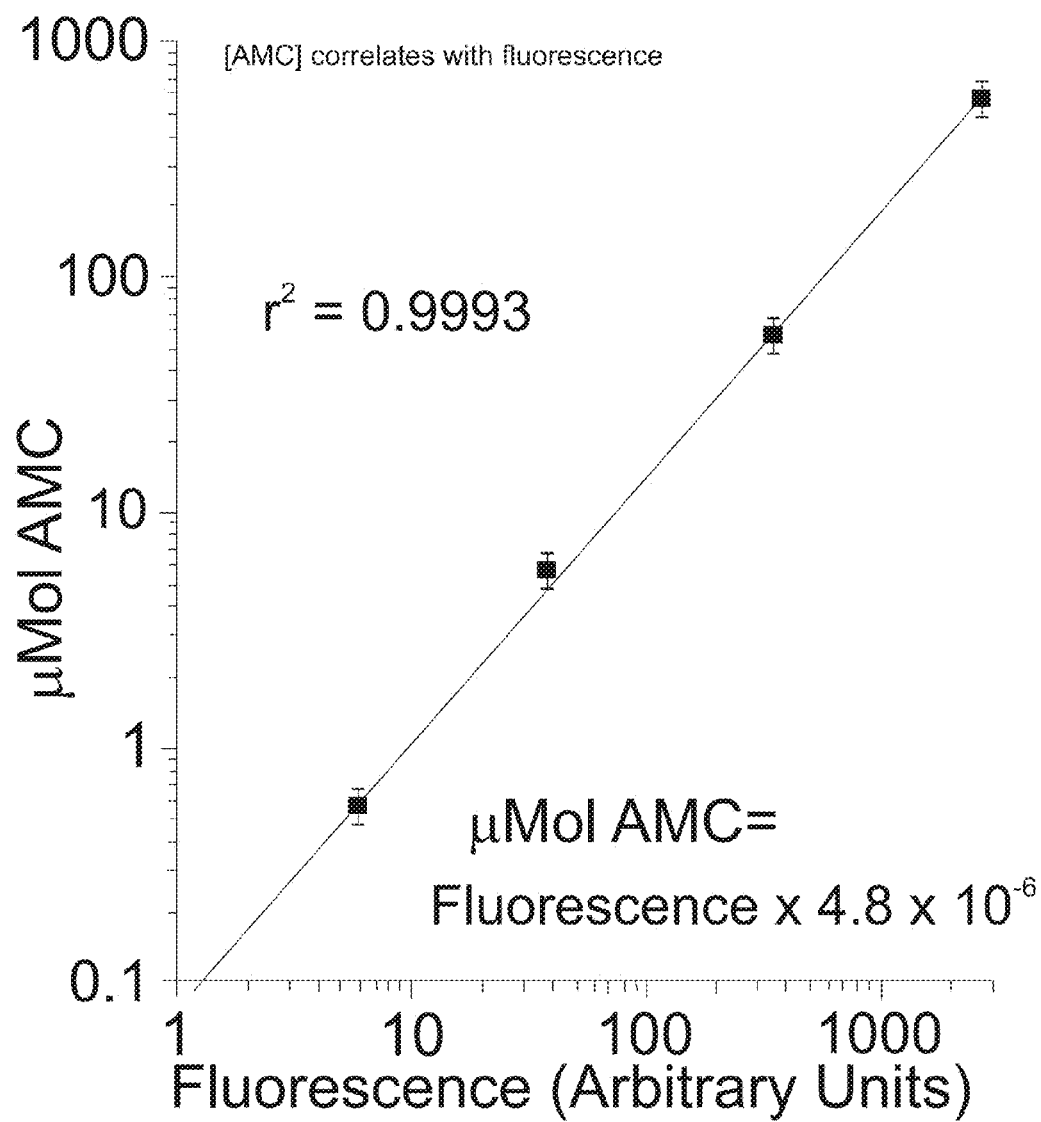
FIG. 2. AMC can be conjugated to free Carboxyl groups on Proteins (A) Linear correlation between free AMC concentration, from 100 nM to 1 mM, and fluorescence. Here different concentrations of AMC, dissolved in proteolysis buffer, were incubated at 37° C. on 96-well plates. Fluorescence was analyzed at an emission wavelength of 444 nM, with excitation wavelength of 390 nm (nanometers). Values are means±SE, n=3. (B) Addition of increasing amounts of BSA to AMC in the presence of NaCNBH3 progressively quenches the fluorescence of AMC. Here 0-50 mg of BSA was added to 100 μM AMC and 20 mM NaCNBH3 and incubated for 1 hr at 37° C. Free AMC content was determined with reference to a standard curve of known AMC concentrations. Values are means±SE, n=3. (C) Here 50 mg/ml of BSA was incubated with 1 mM AMC in the presence or absence of 20 mM NaCNBH3, and then run on a 12% SDS Page gel. A fluorescent BSA-AMC complex was readily observed at ≈66 kDa (the approximate size of BSA), using an excitation wavelength of 365 nM and an emission wavelength of 444 nm, when all three reagents were present, but could only be faintly discerned in the absence of NaCNBH3. A silver stain was later performed. (D) N-(3-Dimethylaminopropyl)-N'-ethylcarbodiimide (1 ng/ml to 100 μg/ml) which blocks free carboxyl groups, was incubated with 50 mg of BSA for 1 hr. BSA was extensively dialyzed then prepared as in panel (C). Increasing concentrations of N-(3-Dimethylamineopropyl)-N'-ethylcarbodiimide, caused a progressive decrease in BSA's electrophoretic mobility, and loss of fluorescence at 66 kDa; a representative gel is shown to the left of the panel, and fluorescence is quantified in the graph to the right.
Figure 2B:
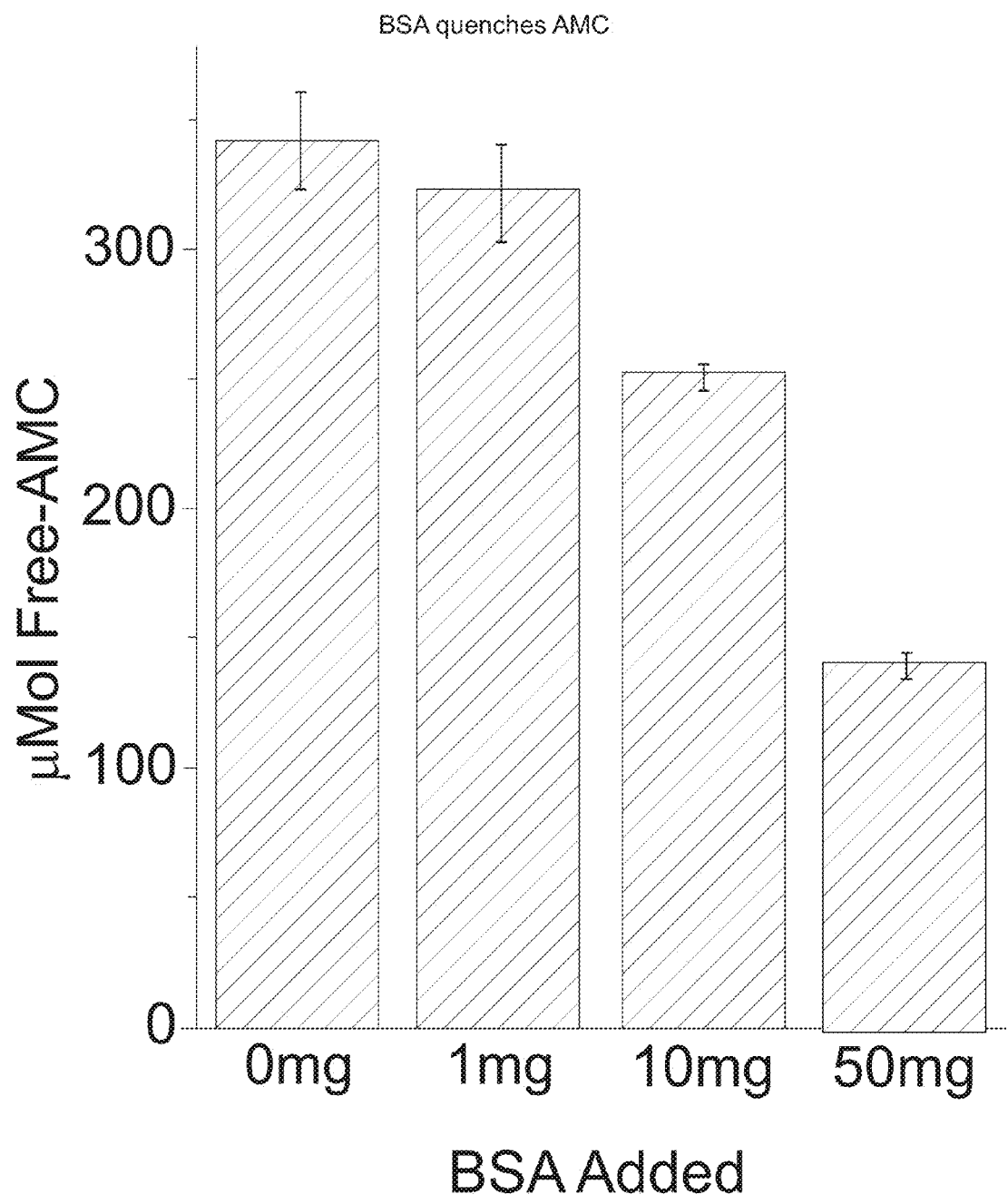

A substantially linear correlation is observed between the concentration of free AMC in solution and the related fluorescence (FIG. 2A), enabling the conversion of fluorescence readings directly to AMC concentrations. It is predicted that incubation of AMC with the protein BSA and the reducing agent $NaCNBH_3$ should result in a reductive labeling reaction, in which the AMC label becomes attached to carboxyl groups on the protein. Binding to proteins could be expected to quench AMC fluorescence. To test this, AMC was incubated with increasing concentrations of BSA in the presence of $NaCNBH_3$ (FIG. 2B) revealing a BSA concentration-dependent loss of fluorescence.

Figure 2C:
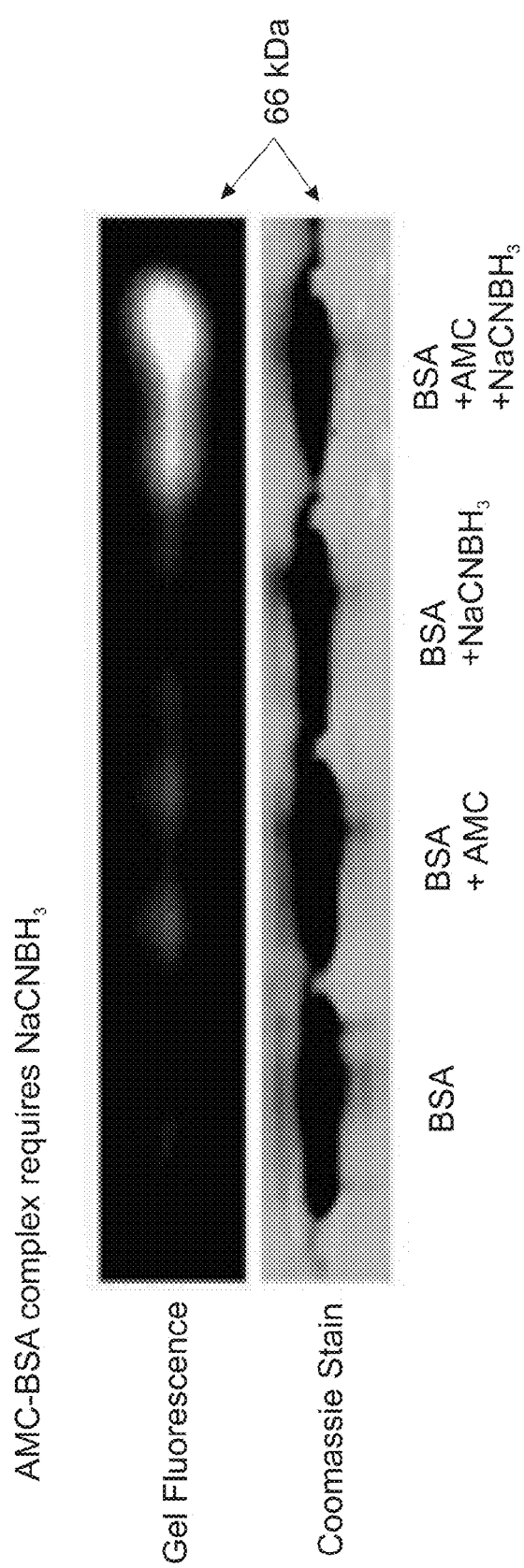
Figure 2D:
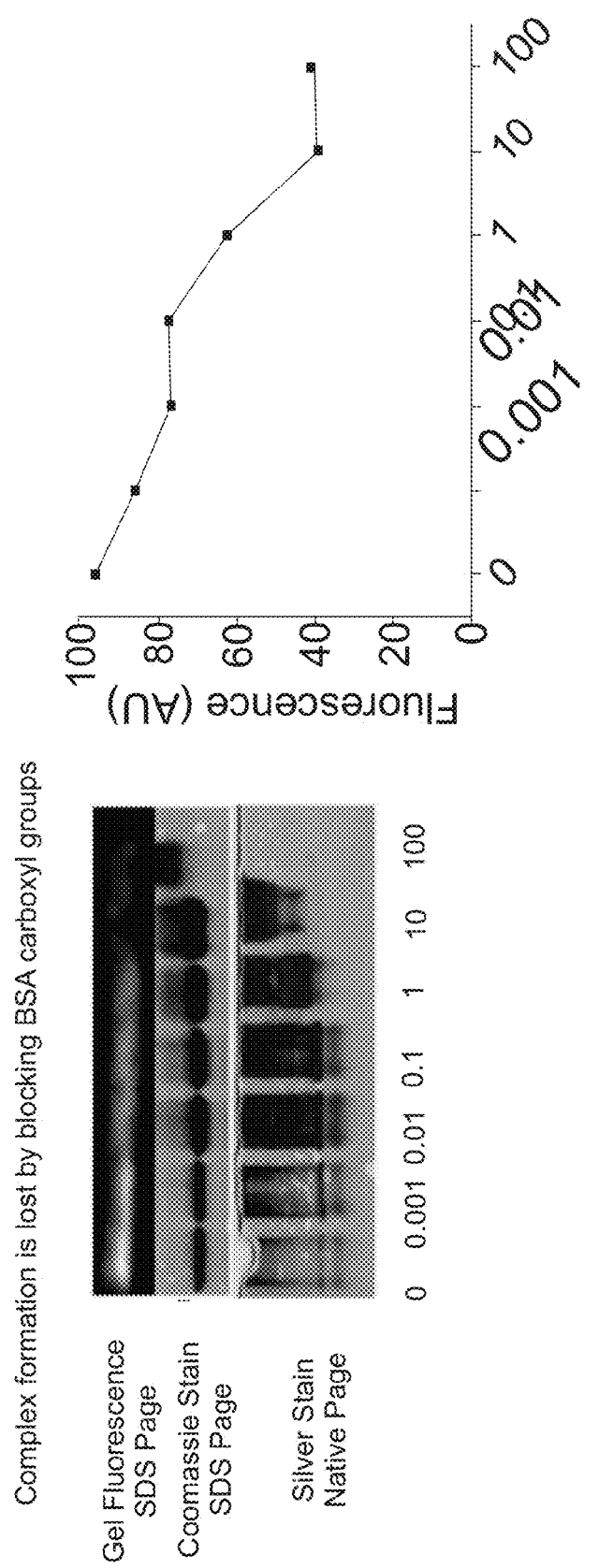

To determine whether binding was actually occurring, SDS-PAGE of BSA treated with AMC±$NaCNBH_3$ (FIG. 2C) was performed. A very weakly fluorescent band was observed at the molecular size of BSA (≈66 kDa) when AMC was incubated with BSA, but a much stronger 66-kDa fluorescent band was seen when the protein was reacted with both AMC and $NaCNBH_3$ together. This implies that the binding of fluorophore to protein requires a reductive step. It is also clear that although protein bound AMC can be detected by fluorescence, the fluorescence yield (brightness) of protein-bound AMC is only a fraction of that seen with free AMC. To test if AMC actually binds to free carboxyl groups, as hypothesized, we incubated 50 mg of BSA with 1 ng-100 g of N-(3-dimethylaminopropyl)-N'-ethylcarbodiimide, which effectively blocks exposed carboxyl groups. After 1 h of incubation we extensively dialyzed samples to remove any free N-(3-dimethylaminopropyl)-N'-ethylcarbodiimide and then attempted to react the BSA with AMC and NaCNBH3. Both SDS-PAGE and native gels of BSA showed clear proof of dose-dependent protein carboxyl-group blocking by N-(3-dimethylaminopropyl)-N'-ethylcarbodiimide, as evidenced by decreased electrophoretic mobility, as the protein became progressively more electropositive with treatment. The same carboxyl-blocking conditions prevented the formation of BSA-AMC adducts, as shown by gradual loss of the fluorescent band at 66 kDa (FIG. 2D and quantified in FIG. 2E).

To test whether exposed amine groups on the protein might react with the carboxyl group on the fluorophore, we used 0.5-50 mM sulfo-NHS-acetate was used to block exposed amine groups on BSA. Despite blocking the majority (80%) of free amine groups we saw no significant change in the fluorescence of the BSA-AMC complex. This implies that the complex formed between AMC and BSA is independent of exposed protein amine groups.

Another possibility was that AMC might be sequestered in protein hydrophobic pockets by non-covalent interactions. To test this, a competition experiment with tryptamine was performed to compete with AMC for non-covalent binding sites on the protein, and measured the effect of tryptamine on quenching of AMC by BSA. The ability of the BSA/AMC complex to function as a substrate for proteolysis was also tested. Despite using a 100 fold excess of tryptamine (at which concentration, protein structure was probably disrupted) only above 30% of the association between AMC and BSA was blocked, and tryptamine had minimal effects on the effectiveness of BSA as a proteolytic substrate. These results imply that non-covalent interactions do not play a significant role in AMC binding to proteins.

Figures 3A, 3B:
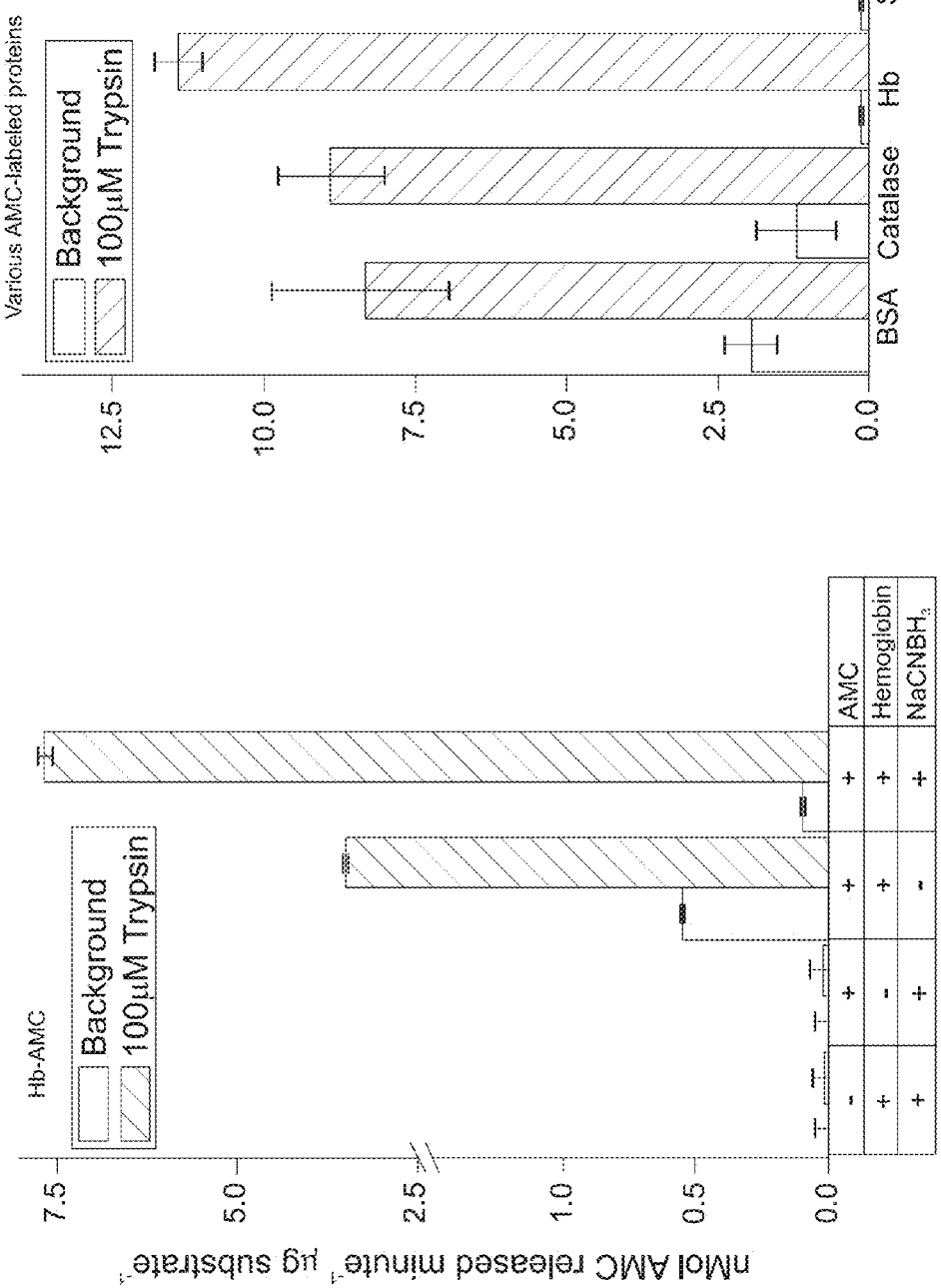
FIG. 3. Proteolysis of AMC-labeled Proteins by Trypsin. (A) Incubation of 1 mg/ml of hemoglobin with 100 μM AMC and 20 mM NaCNBH4 followed by extensive dialysis produced a stable and sensitive substrate for measuring the protease activity, in which 10 μg/ml of Hb-AMC was combined with 10 μM of trypsin. Free AMC content was determined with reference to a standard curve of known AMC concentrations. Values are means±SE's, n=3. (B) AMC labeling of BSA, catalase, Hb, or superoxide dismustase (SOD) generates valid substrates substrates for trypsin digestion, as measured by liberation of fluorescent AMC. All assay conditions (including trypsin concentration) were identical to those in A, and each substrate protein was used at a final concentration of 10 μg/ml. Free AMC content was determined with reference to a standard curve of known AMC concentrations. Values are means±SE's, n=3.

Next, Hb was incubated with $NaCNBH_3$ alone, AMC alone, or AMC and $NaCNBH_3$ then extensively dialyzed the samples to remove any Free AMC or $NaCNBH_3$. As with BSA-AMC (above) it was found that Hb formed a stable adduct with AMC (FIG. 3A). To further test the versatility of the labeling process, the above experiments were repeated using hemoglobin (Hb), catalase, and superoxide dismutase (SOD) as substrates and obtained essentially the same results, generating stable AMC-protein adducts (FIG. 3B).
Utility of AMC-Labeled Proteins as Proteolytic Substrates The Hb-AMC substrate was incubated with the protease trypsin to determine its usefulness as a proteolytic substrate (FIG. 3A). Trypsin released an extremely large amount of AMC fluorophore from Hb, removing any remaining doubt that the fluorophore had actually been successfully adducted to the protein. Reaction of Hb with AMC alone produced a Hb-AMC proteolytic substrate with high background release of AMC, and about a six-fold increase in AMC liberation following incubation with trypsin. In contrast, use of the full labeling procedure, with $NaCNBH_3$ to increase the strength of the adduct, produced a more stable Hb-AMC proteolytic substrate with only one-sixth the background AMC release, but with an 80-fold increase in AMC liberation after trypsin digestion (FIG. 3A). To test the broad applicability of the AMC labeling technique to measure degradation of proteins in general, the AMC fluorophore was bound to BSA, catalase, hemoglobin (Hb), and superoxide dismutase (SOD), and observed that all of the AMC-labeled proteins were effective and sensitive substrates for proteolysis by trypsin, as measured by release of fluorescent AMC (FIG. 3B).

Figure 4A:
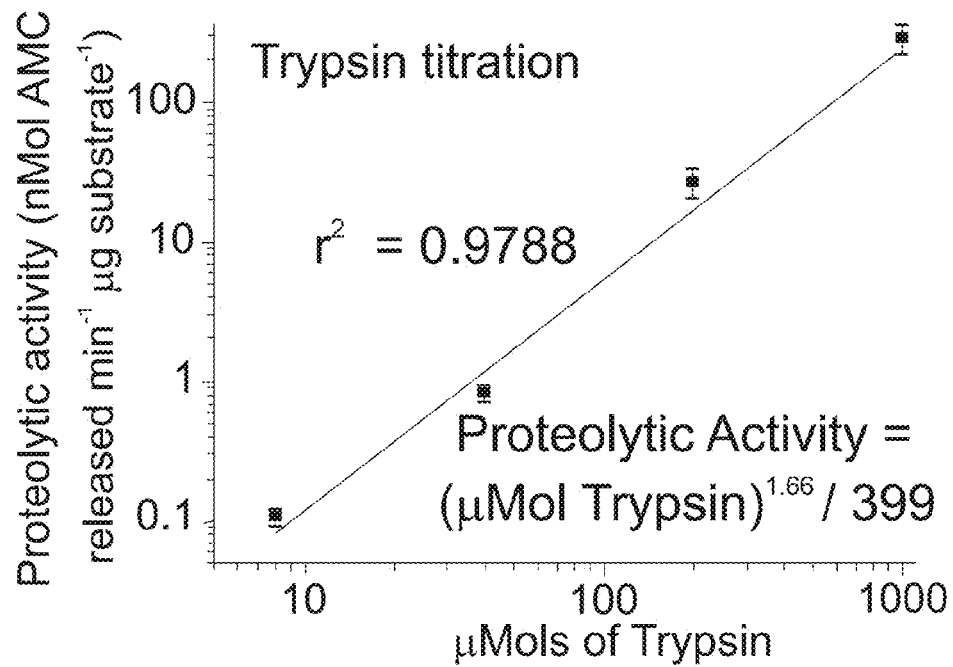
FIG. 4. Protease and Substrate Titration, and Particle Size of Proteolytic Degradation Products. (A) A linear relationship between the concentration of protease and AMC release is seen at trypsin concentrations between 320 nM-1 mM, using an Hb-AMC protein concentration of 10 µg/ml. (B) A linear relationship between the concentration of Hb-AMC substrate and proteolytic activity (AMC release) is seen between 25 ng-2.5 µg of Hb-AMC All other conditions in both Panels A and B were as described in the legend to FIG. 4 and, in both panels, values are means±SE's, n=3. (C) Dialysis of partially digested Hb-AMC substrate shows that the majority of liberated fluorescent AMC-products consist of particles smaller than 500 Da. For this experiment, Hb-AMC (10 µg/ml) was incubated with 10 µM trypsin at 4° C. for 24 hr in dialysis tubing, to generate sufficient fluorescent products to measure, but also to preclude complete digestion of the substrate. Values are means±SE's, n=4, for which the fluorescence of controls was subtracted. (D) Hb was labeled with AMC, or with tritium, by reductive labeling in both cases, as described in Materials & Methods. Protein degradation was measured in panel (A) by AMC fluorescence, and in panel (B) by release of acid-soluble [3H] counts by liquid scintillation, as described in Materials & Methods. Background fluorescence or radioactivity were measured in the absence of protease (proteolysis buffer alone), and proteolysis was measured by increased fluorescence or acid-soluble radioactivity after incubation with either 10 µM Trypsin, 1 µg/ml purified 20S proteosome, or 150 µg/ml MEF cell lysate. Percent degradation of Hb-AMC is reported as the percentage of total fluorescence that could be released from Hb-AMC after exhaustive proteolytic digestion (not shown), whereas percent degradation of [3H]Hb is reported as the percent of total (initial) radioactive counts released into TCA-soluble form by proteolysis. All values are means±SE's, n=3.
Figure 4B:
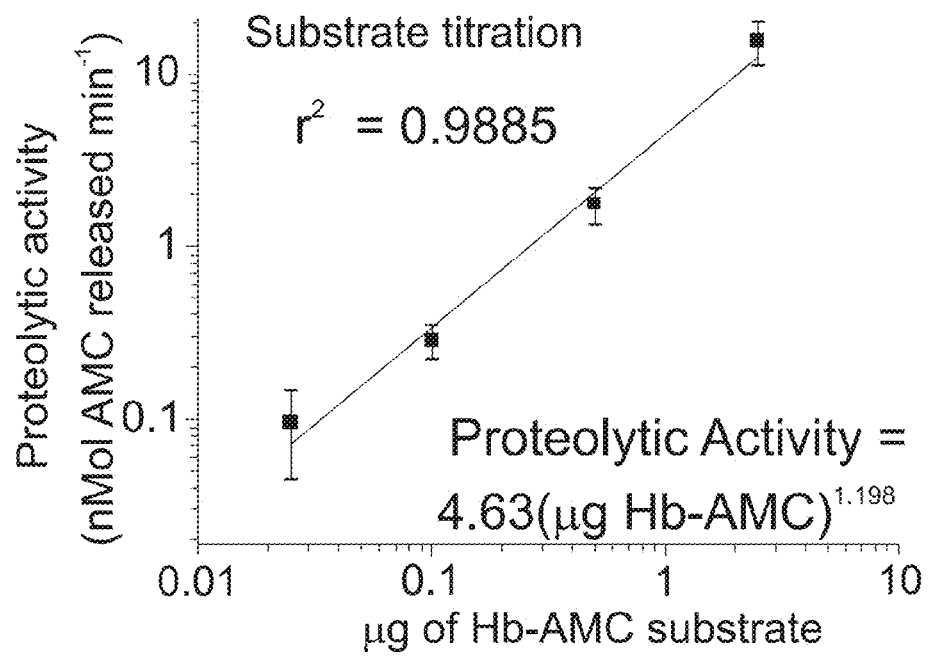

Effective and reliable proteolytic substrates exhibit linear increases in degradation when exposed to linear increases in protease concentration (at least over a fairly wide and useful range), and when substrate concentration is increased in the presence of non-limiting protease activity. To determine the usefulness and reliability of AMC-labeled protein substrates, AMC release was assayed over a wide range of trypsin concentrations and a wide range of substrate concentrations, using Hb-AMC as a model substrate. A linear relationship between proteolytic activity (AMC liberation) and trypsin concentration is observed between 320 nM-1 mM trypsin concentrations (FIG. 4A), and 25 ng-2.5 µg of Hb-AMC substrate (FIG. 4B), when plotted using log-log scales. With these results, linear regression curves with correlation coefficients close to unity are able to be plotted thereby indicating excellent statistical reliability.

Figure 4C:
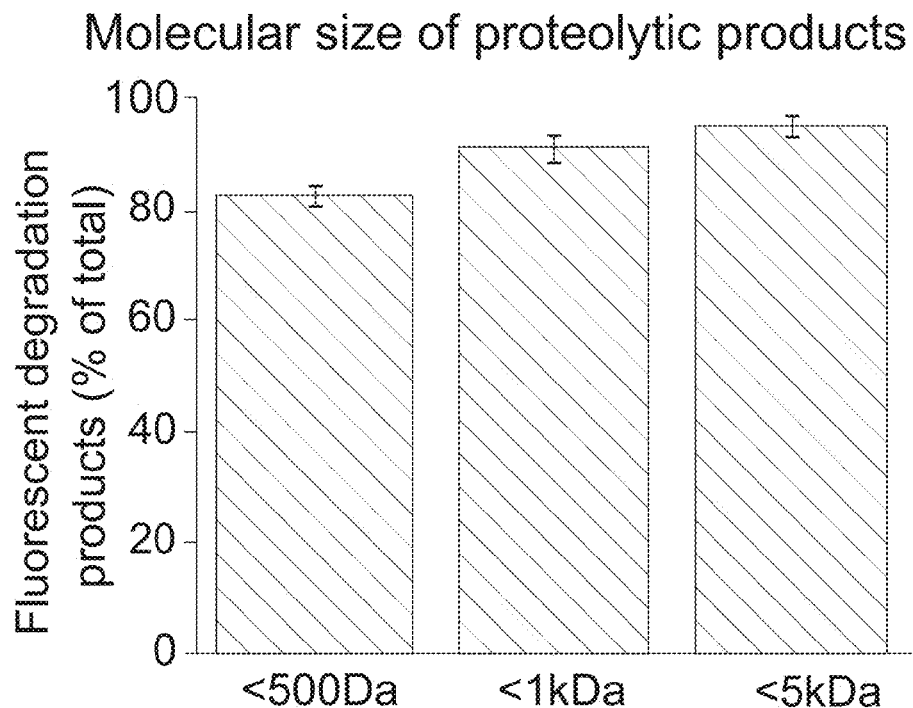

At this point it is clear that free AMC is strongly fluorescent whereas the fluorescence of protein-bound AMC is mostly (but not completely) quenched, and that trypsin-mediated AMC release from AMC-labeled proteins reflects protein degradation. The size(s) of protein-AMC degradation products that actually produce fluorescent signals were determined by partially digesting a sample of Hb-AMC. The sample was then dialyzed through <5 kDa, <1 kDa and <500 Da size exclusion membranes into a 500× volume of proteolysis buffer. Dialysis through a 500 Da filter caused an ≈80% reduction in signal, compared to a ≈90% reduction with a 1 kDa filter and a ≈95% reduction with a 5 kDa filter (FIG. 4C). From this, it is concluded that the majority (80%) of fluorescent products are smaller than 500 Da, while another 15% are particles between 500 Da and 5 kDa, and only some 5% of the signal comes from peptides larger than 5 kDa. These results seem quite consistent with proteolysis assays using radio-labeled protein substrates, in which a TCA precipitation step is routinely used to precipitate remaining intact protein, and peptides larger than about 5 kDa, so that soluble radioactivity reflects free amino acids and only very small peptides. (Grune, T.; Reinheckel, T.; North, J. A.; Li, R.; Bescos, P. B.; Shringarpure, R.; Davies, K. J. A. *Ezrin turnover and cell shape changes catalyzed by proteasome in oxidatively stressed cells*. FASEB J. 16:1602-1610; 2002; the entire disclosure of which is hereby incorporated by reference).

Figure 4D:
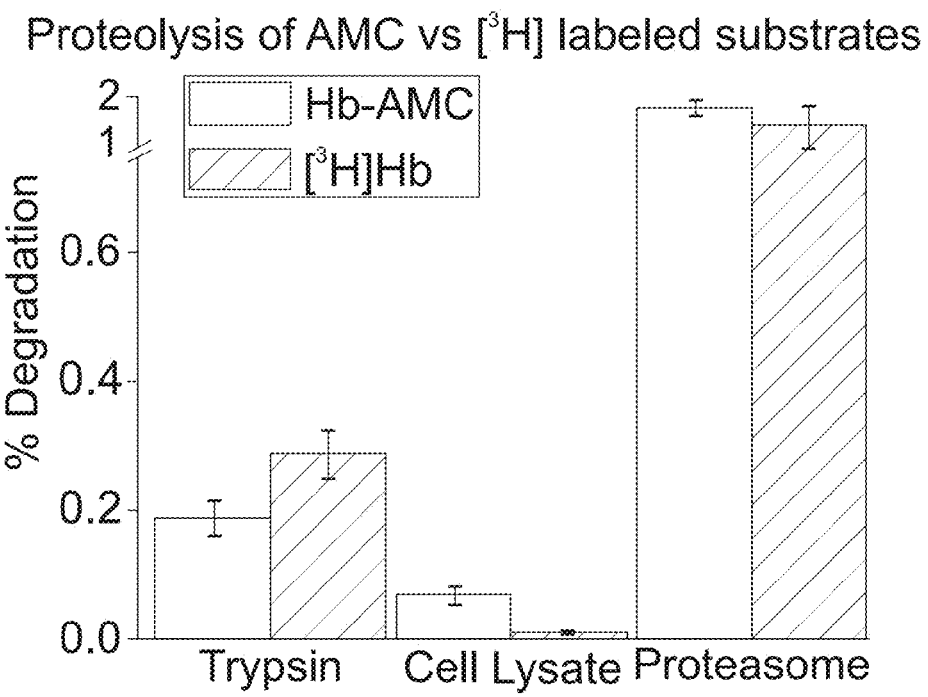
Figure 5A:
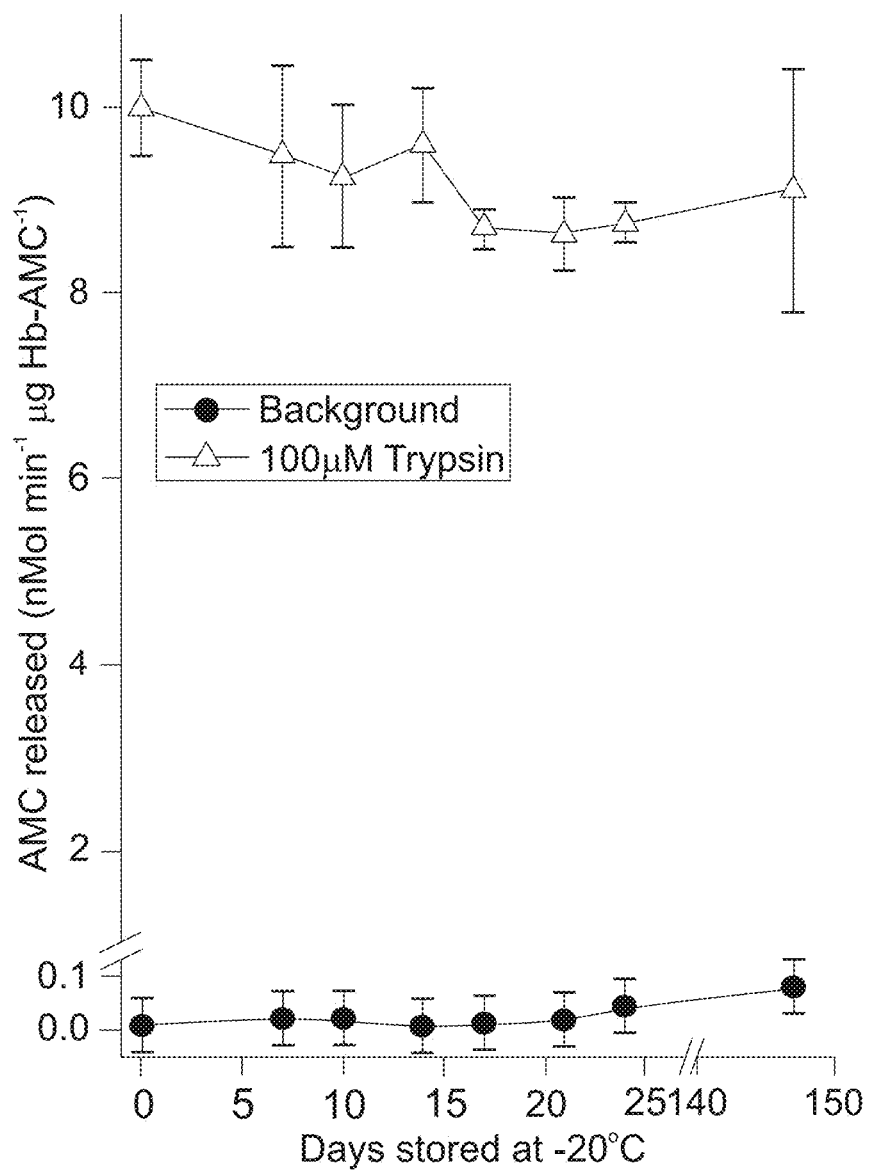
FIG. 5. Stability of AMC-labeled Hemoglobin After Frozen Storage or Denaturation. (A) Hb-AMC was stored at −20° C. for up to 21 weeks. At various time points, samples were thawed, and measurements of both background fluorescence (release of free AMC from the Hb-AMC complex) and liberation of fluorescent AMC by proteolytic digestion with trypsin were measured, as described in FIG. 4A. (B) The stability of Hb-AMC was tested with repeated −20° C. freeze-thaw cycles, by measuring release of free AMC from the Hb-AMC complex (background fluorescence). (C) Hb-AMC was incubated for 60 minutes in dilute HCl at pH 4, 10% 2-mercaptoethanol, 70% methanol, 1 mM peroxynitrite, or 1 mM H2O2, or was boiled at 100° C. for 60 minutes or subjected to free-thawing at −80° C. Release of free AMC from the Hb-AMC complex (background fluorescence) was then measured in comparison with control (untreated Hb-AMC). In all three panels, values are means±SE's, n=3.
Figure 5B:
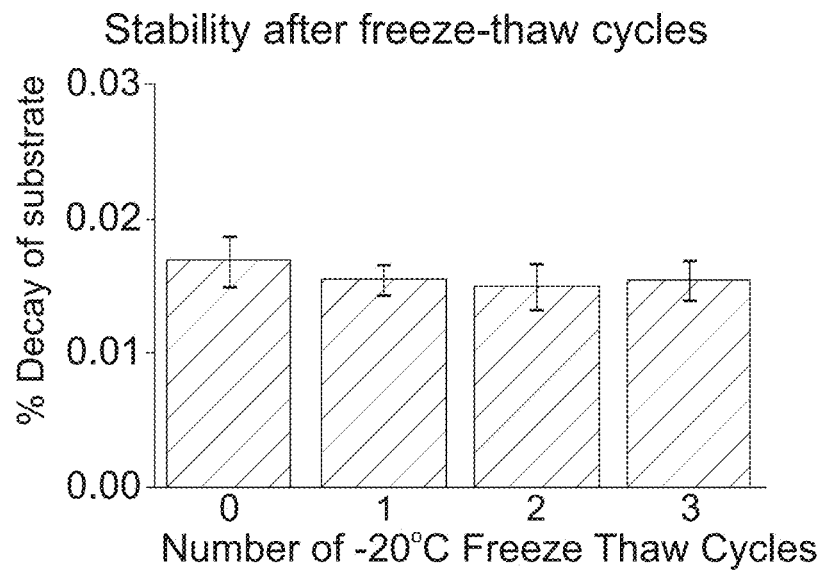

The sensitivity of proteolytic measurements using the AMC-labeled substrates was compared with that of traditional radio-labeled substrates by assessing the degradation of Hb-AMC versus [³H]Hb following incubation with various, widely studied proteolytic systems. The results reveal broadly comparable sensitivity for both substrates, with trypsin, MEF cell lysates, and purified 20S proteasome (FIG. 4D).
Stability of AMC-Labeled Proteins and Resistance to Denaturing Agents The stability of AMC-labeled substrates, the resistance of the AMC-protein linkage to various treatments, and the reproducibility of proteolytic assays after prolonged storage are important concerns in weighing the usefulness of the technique of various embodiments of the present invention. To begin to test these matters, Hb-AMC was stored at −20° C.

and then periodically thawed samples and analyzed both their background release of free AMC (representing undesirable breakdown of the complex) and their proteolytic susceptibility during incubation with trypsin. In repeated trials over 150 days, both the background AMC release, and the trypsin-induced release of AMC varied by less than 15%, indicating that the substrate was quite stable and that samples can be stored for long period of time without significant changes in proteolytic susceptibility (FIG. 5A). As a harsher test of substrate stability, Hb-AMC was subjected to repeated freeze thaw cycles and then measured background release of free AMC (FIG. 5B). This did not significantly affect the stability of the Hb-AMC complex.

Figure 5C:
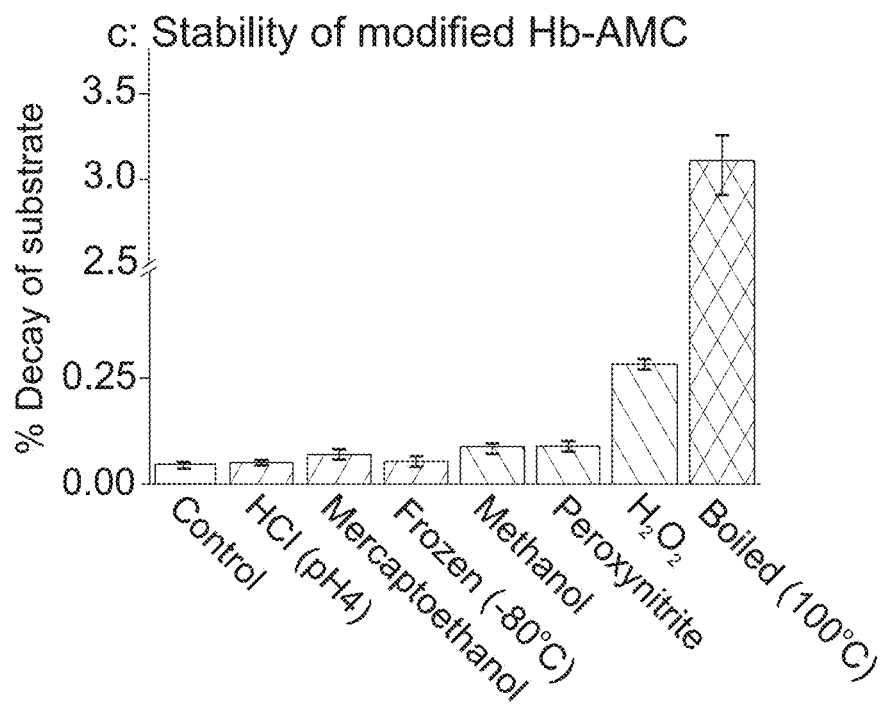

Embodiments of the present invention provide a new way to label proteins for studies of oxidation-induced changes in proteolytic susceptibility. In addition to oxidants, proteolytic substrates are often subjected to various other modifying or denaturing conditions, to test for effects on proteolytic susceptibility, therefore it is important to test the stability of AMC-labeled substrates over a range of harsh conditions. Hb-AMC was almost completely stable to incubation in 1 mM $H_2O_2$, 1 mM peroxynitrite, dilute HCl at pH 4, 10% 2-mercaptoethanol, freeze-thawing at $-80°$ C., or exposure to 50% methanol. Even boiling ($100°$ C.) for 60 minutes only caused a 3.1% breakdown of the Hb-AMC complex (FIG. 5C).

Use of AMC-Labeled Protein Substrates with Acidic, Neutral, and Alkaline Proteases While many proteolytic enzymes have pH optima in the neutral to slightly alkaline range, others are 'designed' to function under strongly acidic or alkaline conditions. We, therefore, needed to test both the fluorescent properties of free AMC over a wide pH range, as well as the stability of protein-AMC complexes. The fluorescence of free AMC was unaffected by mildly acidic or alkaline conditions in a broad range from pH 3-11; highly acidic (below pH 2) or alkaline (above pH 11) conditions, however, significantly decreased AMC fluorescence (FIG. 6A). It should be noted that the fluorescence quenching effects of strong acid or base were completely reversed, with AMC fluorescence returning to normal levels, when pH was neutralized (not shown, but evident in the experiments of FIG. 6B below).

The stability of protein-AMC adducts over the same broad range of pH was determined. For these experiments, Hb-AMC was incubated for 4 hr, using the same pH conditions as in FIG. 6A, after which the pH of each sample was readjusted to pH 7.8 to assess the stability of the Hb-AMC complex, independent of any possible quenching effects of pH on the fluorophore. The Hb-AMC complex was found to be highly stable over the entire range from pH 1-12, with less than a 0.2% decrease in stability observed under any condition (FIG. 6B). The viability of protein-AMC complexes as substrates for proteases was tested with widely different pH optima. As shown in FIG. 6C, Hb-AMC proved to be an excellent substrate for proteolysis with enzymes as diverse as pepsin at pH 2, proteinase K at pH 11, and trypsin or chymotrypsin at pH 7.8.

Use of AMC-Labeling to Detect the Preferential Degradation of Modified Proteins

While digestive enzymes such as trypsin, chymotrypsin, and elastase are very efficient at degrading both normal and modified proteins, major intracellular proteolytic enzymes, such as the Proteasome and the mitochondrial Lon protease exhibit little activity against normal proteins while avidly degrading their modified or damaged forms. The landmark paper of Jentoft and Dearborn (cited above) demonstrated that reductive methylation is a relatively mild treatment and their work, backed-up by thousands of studies by other researchers in the past 30 years have verified that radio-labeling proteins (by reductive methylation) generates protein substrates that are not extensively modified or denatured. Despite the small size of the AMC fluorophore, it is a concern that AMC labeling of proteins might cause a degree of denaturation that would increase the proteolytic susceptibility of normal proteins, making it harder to determine if intentional (experimental) modifications to proteins, such as oxidation, affect their degradation. For a labeling technique to be useful in this regard, one would hope to see only minor degradation of the 'normal' labeled protein but significantly increased degradation of a suitably modified or denatured form by intracellular proteases.

To test this, both control and oxidized forms of Hb-AMC and BSA-AMC were incubated with purified 20S proteasome which selectively degrades oxidized proteins. (Davies, K. J. A. *Degradation of oxidized proteins by the 20S proteasome.* Biochimie 83:301-310; 2001; Shringarpure, R.; Grune, T.; Mehlhase, J.; Davies, K. J. A. *Ubiquitin conjugation is not required for the degradation of oxidized proteins by proteasome.* J. Biol. Chem. 278:311-318; 2003; Davies, K. J. A. *Protein damage and degradation by oxygen radicals. I. General aspects.* J. Biol. Chem. 262:9895-9901; 1987; Pacifici, R. E.; Davies, K. J. A. *Protein degradation as an index of oxidative stress.* Methods Enzymol. 186:485-502; 1990; the entire disclosure of these references is hereby incorporated by reference).

The results show that the unoxidized forms of BSA-AMC and Hb-AMC were rather poor substrates for the purified proteasome, but BSA-AMC's susceptibility to proteasomal degradation increased some four-fold following mild oxidation with $H_2O_2$, whereas that of Hb-AMC increased by more than 300-fold (FIG. 7A). The oxidation of Hb-AMC by peroxynitrite, and a number of other protein denaturing treatments including, boiling, freezing, low pH, methanol, and 2-mercaptoethanol were also tested. Both untreated (control) Hb-AMC and the variously treated Hb-AMC samples were then incubated with lysates of MEF cells for measurements of proteolysis. Cell lysates and extracts (which contain proteasome and many other intracellular proteolytic enzymes) are widely employed in many studies of intracellular proteolytic susceptibility. Oxidative modification of Hb-AMC, by $H_2O_2$ or peroxynitrite, significantly increased its degradation during (subsequent) incubation with MEF cell extracts, in comparison with unmodified (control) Hb-AMC; similar results were also obtained with other methods of Hb-AMC modification, including boiling, freeze-thawing; or exposure to HCl, methanol, or mercaptoethanol (FIG. 7B).

DISCUSSION

The experiments set forth above describe a novel technique for in vitro protein labeling that is free of radio-isotopes. Although this technique contains a reductive step, it is quite distinct from the radio-labeling procedure originally described in the prior art in which either [$^{14}$C] or [$^{3}$H]formaldehyde forms a covalent linkage with free amino groups on target proteins, using the reducing agent $NaBH_4$ or its milder variant $NaCNBH_3$. In the method of the present invention, the fluorophore AMC is reductively ($NaCNBH_3$) conjugated with free protein carboxyl groups, and no methylation step is involved.

A novel technique is described by which an inexpensive and stable AMC fluorophore-protein complex can be formed both quickly and simply by reductively adducting AMC to free carboxyl groups. This technique is also demonstrated to be applicable to a wide range of protein substrates, and that it can be used to measure proteolytic susceptibility with high sensitivity, comparable to that achieved with radio-labeled proteins. Finally, it is shown that AMC-protein adducts are stable to oxidation and various other denaturing conditions, and can be used to measure the increased proteolytic susceptibility of oxidatively modified proteins, as well as proteins modified by other denaturing treatments. In addition to their utility as proteolytic substrates, AMC-labeled proteins could also be used for any other project requiring sensitive detection of stably labeled proteins.

AMC labeling appears to generate substrates which are comparable to $^3$H or $^{14}$C labeled proteins in terms of versatility, stability and reproducibility, and which have several advantages over radiolabeling in terms of safety, labor and cost. Radio-isotopes can be hazardous to use, costly to store or discard, and require complicated and time-consuming training and use permits. Proteolysis assays with radio-labeled substrates require an acid precipitation and centrifugation step (to precipitate undegraded proteins) before sample supernatants are transferred to scintillation vials to quantify $^3$H or $^{14}$C release. These steps are highly work-intensive and error-prone, are a limit to sample numbers, and preclude continuous monitoring of individual samples over time. In comparison, fluorescence assays with AMC-labeled proteins can be easily performed on 96-well plates, with no TCA precipitation or centrifugation, and with continuous monitoring of proteolytic activity over (real) time.

AMC is relatively cheap, compared with radio-labeled formaldehyde. This makes the labeling process approximately 40 times cheaper than $^3$H or $^{14}$C labeling (based on label usage in FIG. 4c). The labeling procedure is also fast and easy, and requires no specialized equipment or training. These factors will now make it feasible for researchers to generate, store, and study whole libraries of labeled protein substrates. Finally, AMC's fluorescent properties, and the AMC-protein bond are stable to oxidation, boiling, freezing, and other modifying or denaturing conditions, while the protein itself can still be modified. Thus AMC-labeled proteins can be used to measure changes in proteolytic susceptibility following oxidation, or any number of other protein modifying treatments.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for measuring degradation of intact proteins, the method comprising:
   a) reductively attaching 7-amino-4-methylcoumarin (AMC) to a protein substrate with a reducing agent, the reducing agent being sodium cyanoborohydride (NaCNBH$_3$) to form an AMC attached protein;
   b) contacting in a test solution the AMC attached protein substrate with a proteolytic enzyme that degrade the protein substrate into protein fragments; and
   c) measuring fluorescence during degradation of the AMC attached protein substrate.

2. The method of claim 1 wherein the fluorescence measured in step c) is compared to a standard curve of known concentration of free AMC to quantify moles of AMC released into solution.

3. The method of claim 2 wherein the known concentration of free AMC is between 5 nM and 5 mM.

4. The method of claim 1 wherein the protein substrate is a purified proteolytic enzyme.

5. The method of claim 1 wherein the protein substrate is obtained from cell lysates or cell extracts.

6. The method of claim 1 wherein the protein substrate has a molecular weight from about 10 kDa (kilodalton) of about 300 kDa.

7. The method of claim 1 wherein the protein substrate is selected from the group consisting of bovine serum albumin (BSA), catalase, hemoglobin, and superoxide dismutase.

8. The method of claim 1 wherein the test solution has a pH from about 2 to about 11.

9. The method of claim 4 wherein the proteolytic enzyme is present in an amount from about 320 nM to about 1 mM of the test solution.

10. The method of claim 1 wherein the protein substrate is present in the test solution in an amount from about 25 ng per milliliter to about 0.5 μg per milliliter.

11. The method of claim 1 wherein greater than 50 percent of the protein fragments are smaller than 500 Da.

12. The method of claim 4 wherein the proteolytic enzyme is selected from the group consisting of pepsin, proteinase K, trypsin, and chymotrypsin.

13. The method of claim 1 wherein the fluorescence is initiated by excitation with light having a wavelength from 360 to 420 nanometers.

14. The method of claim 13 wherein the fluorescence is measured at a wavelength from about 430 to about 450 nanometers.

15. The method of claim 14 wherein the fluorescence is measured at a wavelength of about 444 nanometers.

16. The method of claim 12 wherein the fluorescence is measure at a predetermined time interval.

17. A method for measuring degradation of intact proteins, the method comprising:
   a) reductively attaching coumarin derivative to a protein substrate with a reducing agent, the reducing agent being sodium cyanoborohydride (NaCNBH$_3$) the coumarin derivative having the following formula:

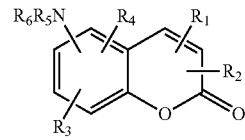

wherein:
   $R_1$, $R_2$ are each independently hydrogen, $C_{1-10}$ alkyl, $C_{1-10}$ alkoxy, $C_{3-10}$ amide, $C_{4-10}$ diamide, $C_{3-10}$ ester, $C_{4-10}$ diester, $C_{6-10}$ aryl, or $C_{6-10}$ heteroaryl;
   $R_3$, $R_4$ are each independently hydrogen, $C_{1-10}$ alkyl, $C_{1-10}$ alkoxy, $C_{2-10}$ carboxy, $C_{3-10}$ amide, $C_{4-10}$ diamide, $C_{3-10}$ ester, $C_{4-10}$ diester, $C_{6-10}$ aryl, or $C_{6-10}$ heteroaryl; and
   $R_5$, $R_6$ are each independently hydrogen or $C_{1-5}$ alkyl;
   b) contacting in a test solution the protein substrate with a proteolytic enzyme that degrade the protein substrate into protein fragments; and
   c) measuring fluorescence during degradation of the protein substrate.

18. The method of claim 17 wherein $R_5$, $R_6$ are each independently hydrogen.

19. The method of claim 18 wherein $R_1$ is $C_{1-10}$ alkyl, $C_{1-10}$ alkoxy, or $C_{1-10}$ perfluoroalkyl and $R_2$, $R_3$, $R_4$ are hydrogen.

* * * * *